United States Patent
Lim et al.

(10) Patent No.: US 10,155,765 B2
(45) Date of Patent: Dec. 18, 2018

(54) CARBOXAMIDE INHIBITORS OF IRAK4 ACTIVITY

(71) Applicant: MERCK SHARP & DOHME CORP., Rahway, NJ (US)

(72) Inventors: Jongwon Lim, Lexington, MA (US); Michael D. Altman, Needham, MA (US); Matthew L. Childers, Medfield, MA (US); Craig R. Gibeau, Holliston, MA (US); Ginny Dai Ho, Murray Hill, NJ (US); Honchung Tsui, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/557,195

(22) PCT Filed: Mar. 7, 2016

(86) PCT No.: PCT/US2016/021116
§ 371 (c)(1),
(2) Date: Sep. 11, 2017

(87) PCT Pub. No.: WO2016/144844
PCT Pub. Date: Sep. 15, 2016

(65) Prior Publication Data
US 2018/0051027 A1 Feb. 22, 2018

Related U.S. Application Data

(60) Provisional application No. 62/132,183, filed on Mar. 12, 2015.

(51) Int. Cl.
| | |
|---|---|
| *C07D 487/04* | (2006.01) |
| *A61K 45/06* | (2006.01) |
| *C07D 495/04* | (2006.01) |
| *A61K 31/4985* | (2006.01) |
| *A61K 31/519* | (2006.01) |
| *A61K 31/53* | (2006.01) |
| *A61K 31/5377* | (2006.01) |
| *A61K 31/635* | (2006.01) |

(52) U.S. Cl.
CPC ........ *C07D 487/04* (2013.01); *A61K 31/4985* (2013.01); *A61K 31/519* (2013.01); *A61K 31/53* (2013.01); *A61K 31/5377* (2013.01); *A61K 31/635* (2013.01); *A61K 45/06* (2013.01); *C07D 495/04* (2013.01)

(58) Field of Classification Search
CPC ..................................................... C07D 487/04
See application file for complete search history.

(56) References Cited

U.S. PATENT DOCUMENTS

| | | |
|---|---|---|
| 6,414,013 B1 | 7/2002 | Fancelli et al. |
| 2004/0209886 A1 | 10/2004 | Salvati et al. |
| 2012/0028919 A1 | 2/2012 | Breslin et al. |
| 2014/0194404 A1 | 7/2014 | McElroy et al. |
| 2014/0303149 A1 | 10/2014 | Arora et al. |
| 2015/0005499 A1 | 1/2015 | Haas et al. |

FOREIGN PATENT DOCUMENTS

| | | |
|---|---|---|
| WO | WO2005012256 A1 | 2/2005 |
| WO | WO2013163159 A2 | 10/2013 |

OTHER PUBLICATIONS

Jeffrey J. Mason, Studies of Cephalandole Alkaloids and the Revised Structure of Cephalandole A, Journal of Natural Products, Aug. 1, 2008, 1447-1450, 71-8.

*Primary Examiner* — Paul V Ward
(74) *Attorney, Agent, or Firm* — Matthew A. Leff; Laura M. Ginkel

(57) ABSTRACT

The present invention relates to carboxamide inhibitors of IRAK4 of formula (I) and provides compositions comprising such inhibitors, as well as methods therewith for treating IRAK4-mediated or -associated conditions or diseases.

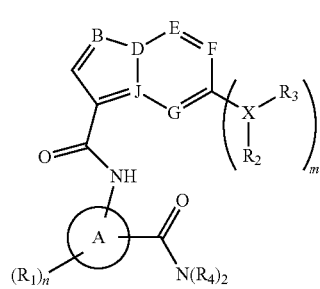

11 Claims, No Drawings

CARBOXAMIDE INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4): 221-237; and O'Neill, Biochem. Soc. Trans., 2000, 28(5): 557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monomyeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to carboxamide inhibitors of IRAK4 of formula (I) and provides compositions comprising such inhibitors, as well as methods therewith for treating IRAK4-mediated or -associated conditions or diseases.

DETAILED DESCRIPTION OF THE INVENTION

The compounds of the instant invention are useful in the inhibition of the activity of IRAK4.

An embodiment of the instant invention is illustrated by the Formula I:

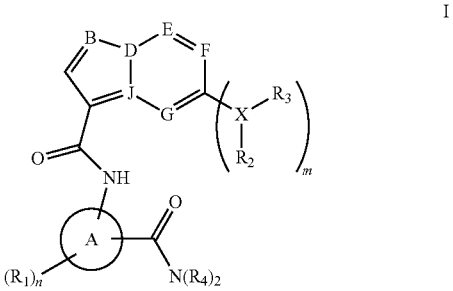

wherein:
B is CH, N or S; D is CH or N; E is CH or N; F is CH or N; G is CH or N; and J is C or N, wherein when B is S then D is CH, E is N, F is CH, G is N and J is C;

X is O, S, $CH_2$ or N;

m is 0 or 1; n is 0, 1 or 2;

Ring A is pyridinyl, pyrazolyl, thiophenyl, furanyl or phenyl, $R_1$ is independently selected from $(C_1\text{-}C_4)$alkyl, pyrimidine, piperidine and phenyl, each optionally substituted with $(C_1\text{-}C_4)$alkyl, OH, halo, $O(C_1\text{-}C_4)$alkyl, methylpiperidine, $S(O)_2R_c$, $C(O)N(R_b)_2$, or $C(O)O(C_1\text{-}C_4)$alkyl;

$R_2$ is absent or H and $R_3$ is independently selected from: $(C_1\text{-}C_4)$alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form piperazine or morpholine each optionally substituted with oxo;

$R_4$ is independently H or methyl;

$R_b$ is independently selected from H and $(C_1$-$C_4)$alkyl; and $R_c$ is methyl;

or a pharmaceutically acceptable salt thereof.

Another embodiment of the instant invention is illustrated by the Formula I: wherein:

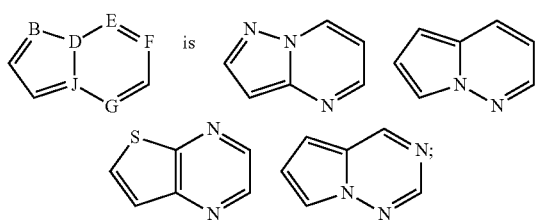

X is O, $CH_2$ or N;

m is 0 or 1; n is 0, 1 or 2;

Ring A is pyridinyl, pyrazolyl, thiophenyl, furanyl or phenyl, $R_1$ is independently selected from $(C_1$-$C_4)$alkyl, pyrimidine, piperidine and phenyl, each optionally substituted with $(C_1$-$C_4)$alkyl, OH, halo, $O(C_1$-$C_4)$alkyl, methylpiperidine, $S(O)_2R_c$, $C(O)N(R_b)_2$, or $C(O)O(C_1$-$C_4)$alkyl;

$R_2$ is absent or H and $R_3$ is independently selected from: $(C_1$-$C_4)$alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form piperazine or morphonline, each optionally substituted with oxo;

$R_4$ is independently H or methyl;

$R_b$ is independently selected from H and $(C_1$-$C_4)$alkyl; and $R_c$ is methyl;

or a pharmaceutically acceptable salt thereof.

Another embodiment of the instant invention is illustrated by the Formula II:

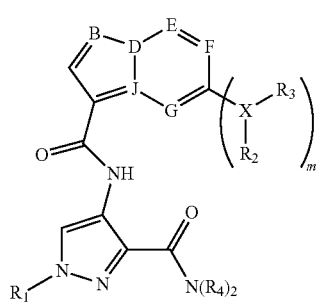

wherein:

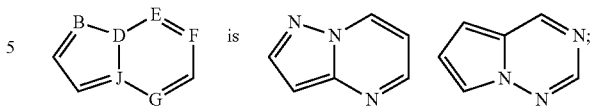

X is O, S, $CH_2$ or N;

m is 0 or 1;

$R_1$ is independently selected from $(C_1$-$C_4)$alkyl, pyrimidine, piperidine and phenyl, each optionally substituted with $(C_1$-$C_4)$alkyl, OH, halo, $O(C_1$-$C_4)$alkyl, methylpiperidine, $S(O)_2R_c$, $C(O)N(R_b)_2$, or $C(O)O(C_1$-$C_4)$alkyl;

$R_2$ is absent or H and $R_3$ is independently selected from: $(C_1$-$C_4)$alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form piperazine or morpholine, each optionally substituted with oxo;

$R_4$ is independently H or methyl;

$R_b$ is independently selected from H and $(C_1$-$C_4)$alkyl; and $R_c$ is methyl;

or a pharmaceutically acceptable salt thereof.

A compound selected from:

5-{[(3R,4R)-4-aminotetrahydro-2H-pyran-3-yl]amino}-N-(3-carbamoyl-1-methyl-1H-pyrazol-4-yl)pyrazolo[1,5-a]pyrimidine-3-carboxamide;

5-{[(3R,4R)-3-aminotetrahydro-2H-pyran-4-yl]amino}-N-(3-carbamoyl-1-methyl-1H-pyrazol-4-yl)pyrazolo[1,5-a]pyrimidine-3-carboxamide;

5-{[(1R,2R)-2-amino-3,3-difluorocyclohexyl]amino}-N-(3-carbamoyl-1-methyl-1H-pyrazol-4-yl)pyrazolo[1,5-a]pyrimidine-3-carboxamide;

5-{[(3S,4S)-3-amino-1,1-dioxidotetrahydro-2H-thiopyran-4-yl]amino}-N-(3-carbamoyl-1-methyl-1H-pyrazol-4-yl)pyrazolo[1,5-a]pyrimidine-3-carboxamide;

5-{[(3R,4R)-4-amino-1,1-dioxidotetrahydro-2H-thiopyran-3-yl]amino}-N-(3-carbamoyl-1-methyl-1H-pyrazol-4-yl)pyrazolo[1,5-a]pyrimidine-3-carboxamide;

5-{[(1S,2R)-2-aminocyclohexyl]amino}-N-(3-carbamoyl-1-pyridin-3-yl-1H-pyrazol-4-yl)pyrazolo[1,5-a]pyrimidine-3-carboxamide;

5-{[(1S,2R)-2-aminocyclohexyl]amino}-N-(3-carbamoyl-1-methyl-1H-pyrazol-4-yl)pyrazolo[1,5-a]pyrimidine-3-carboxamide;

5-{[(1R,2R)-2-aminocyclohexyl]amino}-N-(3-carbamoyl-1-methyl-1H-pyrazol-4-yl)pyrazolo[1,5-a]pyrimidine-3-carboxamide;

5-{[(1R,2S)-2-aminocyclohexyl]amino}-N-(3-carbamoyl-1-methyl-1H-pyrazol-4-yl)pyrazolo[1,5-a]pyrimidine-3-carboxamide;

5-{[(1S,2R)-2-aminocyclohexyl]amino}-N-[3-carbamoyl-1-(1-methylpiperidin-3-yl)-1H-pyrazol-4-yl]pyrazolo[1,5-a]pyrimidine-3-carboxamide;

5-[(2-aminoethyl)amino]-N-(3-carbamoyl-1-pyridin-3-yl-1H-pyrazol-4-yl)pyrazolo[1,5-a]pyrimidine-3-carboxamide;

5-[(2-aminocyclopentyl)amino]-N-(3-carbamoyl-1-methyl-1H-pyrazol-4-yl)pyrazolo[1,5-a]pyrimidine-3-carboxamide;

5-[(2-aminocycloheptyl)amino]-N-(3-carbamoyl-1-methyl-1H-pyrazol-4-yl)pyrazolo[1,5-a]pyrimidine-3-carboxamide;

N-(3-carbamoyl-1-methyl-1H-pyrazol-4-yl)-5-(pyrrolidin-3-ylamino)pyrazolo[1,5-a]pyrimidine-3-carboxamide;

N-(3-carbamoyl-1-methyl-1H-pyrazol-4-yl)-5-(piperidin-3-ylamino)pyrazolo[1,5-a]pyrimidine-3-carboxamide;

5-{[(1S,2R)-2-aminocyclohexyl]amino}-N-[1-methyl-3-(methylcarbamoyl)-1H-pyrazol-4-yl]pyrazolo[1,5-a]pyrimidine-3-carboxamide;

5-{[(1S,2R)-2-aminocyclohexyl]amino}-N-[3-(dimethylcarbamoyl)-1-methyl-1H-pyrazol-4-yl]pyrazolo[1,5-a]pyrimidine-3-carboxamide;

5-{[(1S,2R)-2-aminocyclohexyl]amino}-N-{3-carbamoyl-1-[1-(methylsulfonyl)piperidin-4-yl]-1H-pyrazol-4-yl}pyrazolo[1,5-a]pyrimidine-3-carboxamide;

5-{[(1S,2R)-2-aminocyclohexyl]amino}-N-[3-carbamoyl-1-(1-methylpiperidin-4-yl)-1H-pyrazol-4-yl]-7aH-pyrazolo[4,3-b]pyridine-3-carboxamide;

5-{[(1S,2R)-2-aminocyclohexyl]amino}-N-{3-carbamoyl-1-[1-(methylsulfonyl)piperidin-3-yl]-1H-pyrazol-4-yl}pyrazolo[1,5-a]pyrimidine-3-carboxamide;

5-{[(1R,2S)-2-aminocyclohexyl]amino}-N-(3-carbamoyl-1-ethyl-1H-pyrazol-4-yl)pyrazolo[1,5-a]pyrimidine-3-carboxamide;

5-{[(1R,2S)-2-aminocyclohexyl]amino}-N-[3-carbamoyl-1-(1-methylethyl)-1H-pyrazol-4-yl]pyrazolo[1,5-a]pyrimidine-3-carboxamide;

5-{[(1R,2S)-2-aminocyclohexyl]amino}-N-[3-carbamoyl-1-(2-hydroxyethyl)-1H-pyrazol-4-yl]pyrazolo[1,5-a]pyrimidine-3-carboxamide;

5-{[(1R,2S)-2-aminocyclohexyl]amino}-N-[3-carbamoyl-1-(2-methoxyethyl)-1H-pyrazol-4-yl]pyrazolo[1,5-a]pyrimidine-3-carboxamide;

5-{[(1R,2S)-2-aminocyclohexyl]amino}-N-{3-carbamoyl-1-[(1-methylpiperidin-3-yl)methyl]-1H-pyrazol-4-yl}pyrazolo[1,5-a]pyrimidine-3-carboxamide;

N-(3-carbamoyl-1-methyl-1H-pyrazol-4-yl)-5-(cyclohexylamino)pyrazolo[1,5-a]pyrimidine-3-carboxamide;

N-(3-carbamoyl-1-methyl-1H-pyrazol-4-yl)-5-[(2-hydroxycyclohexyl)amino]pyrazolo[1,5-a]pyrimidine-3-carboxamide;

5-[(2-aminoethyl)amino]-N-(3-carbamoyl-1-methyl-1H-pyrazol-4-yl)pyrazolo[1,5-a]pyrimidine-3-carboxamide;

N-(3-carbamoyl-1-methyl-1H-pyrazol-4-yl)-5-{[(5-oxopyrrolidin-3-yl)methyl]amino}pyrazolo[1,5-a]pyrimidine-3-carboxamide;

N-(3-carbamoyl-1-methyl-1H-pyrazol-4-yl)-5-morpholin-4-ylpyrazolo[1,5-a]pyrimidine-3-carboxamide;

N-(3-carbamoyl-1-methyl-1H-pyrazol-4-yl)-5-piperazin-1-ylpyrazolo[1,5-a]pyrimidine-3-carboxamide;

5-{[(1R,2S)-2-aminocyclohexyl]amino}-N-[1-(2-amino-2-oxoethyl)-3-carbamoyl-1H-pyrazol-4-yl]pyrazolo[1,5-a]pyrimidine-3-carboxamide;

N-{3-carbamoyl-1-[4-(methylsulfamoyl)phenyl]-1H-pyrazol-4-yl}-5-piperazin-1-ylpyrazolo[1,5-a]pyrimidine-3-carboxamide;

N-(3-carbamoyl-1-pyridin-4-yl-1H-pyrazol-4-yl)-5-piperazin-1-ylpyrazolo[1,5-a]pyrimidine-3-carboxamide;

N-(5-carbamoyl-1-pyridin-4-yl-1H-pyrazol-4-yl)-5-piperazin-1-ylpyrazolo[1,5-a]pyrimidine-3-carboxamide;

N-(3-carbamoyl-1-pyridin-3-yl-1H-pyrazol-4-yl)-5-piperazin-1-ylpyrazolo[1,5-a]pyrimidine-3-carboxamide;

N-(3-carbamoyl-1-pyridin-2-yl-1H-pyrazol-4-yl)-5-piperazin-1-ylpyrazolo[1,5-a]pyrimidine-3-carboxamide;

N-(3-carbamoyl-1-methyl-1H-pyrazol-4-yl)-5-(3-oxopiperazin-1-yl)pyrazolo[1,5-a]pyrimidine-3-carboxamide;

5-(2-aminoethoxy)-N-(3-carbamoyl-1-methyl-1H-pyrazol-4-yl)pyrazolo[1,5-a]pyrimidine-3-carboxamide;

5-(3-aminopropyl)-N-(3-carbamoyl-1-methyl-1H-pyrazol-4-yl)pyrazolo[1,5-a]pyrimidine-3-carboxamide;

N-(2-carbamoylpyridin-3-yl)pyrazolo[1,5-a]pyrimidine-3-carboxamide;

N-(3-carbamoyl-1-methyl-1H-pyrazol-4-yl)pyrazolo[1,5-a]pyrimidine-3-carboxamide;

N-(3-carbamoyl-1-methyl-1H-pyrazol-4-yl)pyrrolo[1,2-b]pyridazine-7-carboxamide;

N-(3-carbamoyl-1-pyridin-3-yl-1H-pyrazol-4-yl)pyrazolo[1,5-a]pyrimidine-3-carboxamide;

N-(4-carbamoylpyridin-3-yl)pyrazolo[1,5-a]pyrimidine-3-carboxamide;

tert-butyl 4-{3-carbamoyl-4-[(pyrazolo[1,5-a]pyrimidin-3-ylcarbonyl)amino]-1H-pyrazol-1-yl}piperidine-1-carboxylate;

N-(3-carbamoyl-1-piperidin-4-yl-1H-pyrazol-4-yl)pyrazolo[1,5-a]pyrimidine-3-carboxamide;

N-{3-carbamoyl-1-[1-(methylsulfonyl)piperidin-4-yl]-1H-pyrazol-4-yl}pyrazolo[1,5-a]pyrimidine-3-carboxamide;

N-(3-carbamoylpyridin-4-yl)pyrazolo[1,5-a]pyrimidine-3-carboxamide;

N-(2-carbamoylthiophen-3-yl)pyrazolo[1,5-a]pyrimidine-3-carboxamide;

N-(5-tert-butyl-2-carbamoylthiophen-3-yl)pyrazolo[1,5-a]pyrimidine-3-carboxamide;

N-(2-carbamoylphenyl)pyrazolo[1,5-a]pyrimidine-3-carboxamide;

N-(3-carbamoyl-1H-pyrazol-4-yl)pyrazolo[1,5-a]pyrimidine-3-carboxamide;

N-(2-carbamoyl-5-chloro-4-sulfamoylphenyl)pyrazolo[1,5-a]pyrimidine-3-carboxamide;

N-(4-bromo-2-carbamoylphenyl)pyrazolo[1,5-a]pyrimidine-3-carboxamide;

N-(3-carbamoyl-1-methyl-1H-pyrazol-4-yl)thieno[2,3-b]pyrazine-7-carboxamide;

N-(3-carbamoyl-1-methyl-1H-pyrazol-4-yl)-2-(methylsulfanyl)pyrrolo[2,1-f][1,2,4]triazine-7-carboxamide;

2-[(2-aminoethyl)amino]-N-(3-carbamoyl-1-methyl-1H-pyrazol-4-yl)pyrrolo[2,1-f][1,2,4]triazine-7-carboxamide;

2-[(2-aminoethyl)amino]-N-[3-carbamoyl-1-(2-hydroxyethyl)-1H-pyrazol-4-yl]pyrrolo[2,1-f][1,2,4]triazine-7-carboxamide;

2-[(2-aminoethyl)amino]-N-[1-methyl-3-(methylcarbamoyl)-1H-pyrazol-4-yl]pyrrolo[2,1-f][1,2,4]triazine-7-carboxamide;

2-{[(1R,2S)-2-aminocyclohexyl]amino}-N-(3-carbamoyl-1-methyl-1H-pyrazol-4-yl)pyrrolo[2,1-f][1,2,4]triazine-7-carboxamide;

2-{[(1R,2S)-2-aminocyclohexyl]amino}-N-(3-carbamoyl-1-ethyl-1H-pyrazol-4-yl)pyrrolo[2,1-f][1,2,4]triazine-7-carboxamide;

2-{[(1R,2S)-2-aminocyclohexyl]amino}-N-[3-carbamoyl-1-(2-hydroxyethyl)-1H-pyrazol-4-yl]pyrrolo[2,1-f][1,2,4]triazine-7-carboxamide;

2-{[(1R,2S)-2-aminocyclohexyl]amino}-N-[1-methyl-3-(methylcarbamoyl)-1H-pyrazol-4-yl]pyrrolo[2,1-f][1,2,4]triazine-7-carboxamide;

2-{[(1R,2S)-2-aminocyclohexyl]amino}-N-[1-(2-hydroxyethyl)-3-(methylcarbamoyl)-1H-pyrazol-4-yl]pyrrolo[2,1-f][1,2,4]triazine-7-carboxamide; and 2-{[(1R,2S)-2-aminocyclohexyl]amino}-N-[3-carbamoyl-1-(2-methoxyethyl)-1H-pyrazol-4-yl]pyrrolo[2,1-f][1,2,4]triazine-7-carboxamide;

or a pharmaceutically acceptable salt thereof.

When any variable (e.g. $R_a$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. In some instances, two substituents are attached to the same carbon and come together to form a carbocyclic or heterocyclic ring (a spirocyclic ring system).

As used herein, "alkyl" is intended to include branched, cyclic and straight-chain saturated aliphatic hydrocarbon groups having the specified number of carbon atoms. For example, $C_1$-$C_4$, as in "($C_1$-$C_4$)alkyl" is defined to include groups having 1, 2, 3 or 4 carbons in a linear, cyclic or branched arrangement. For example, "($C_1$-$C_4$)alkyl" specifically includes methyl, ethyl, n-propyl, i-propyl, cyclopropyl, n-butyl, t-butyl, i-butyl and cyclobutyl.

As appreciated by those of skill in the art, "halo" or "halogen" as used herein is intended to include chloro (Cl), fluoro (F), bromo (Br) and iodo (I).

In another embodiment of Formula I, B is N, D is N, E is CH, F is CH, G is N, and J is C.

In another embodiment of Formula I, B is CH, D is N, E is CH, F is CH, G is N, and J is C.

In another embodiment of Formula I or II, Ring A is pyridinyl, pyrazolyl, thiophenyl or phenyl.

In another embodiment of Formula I or II, Ring A is pyrazolyl.

In another embodiment of Formula I or II, X is N.

In another embodiment of Formula I or II, m is 0.

In another embodiment of Formula I or II, m is 1.

In another embodiment of Formula I or II, n is 1.

In another embodiment of Formula I or II, $R_1$ is methyl.

In another embodiment of Formula I or II, $R_2$ is H.

In another embodiment of Formula I or II, $R_3$ is cyclohexyl optionally substituted with $NH_2$.

In another embodiment of Formula I or II, $R_4$ is H.

In another embodiment, halo is Cl, F or Br.

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The IRAK4 inhibitor compounds of the present invention, which can be in the form of a free base, may be isolated from the reaction mixture in the form of a pharmaceutically acceptable salt.

The compounds of Formula I and II can form salts which are also within the scope of this invention. Reference to a compound of Formula I and II herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I and II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The IRAK4 inhibitor compounds of the present invention may exist as amorphous forms or crystalline forms.

The compounds of Formula I and II may have the ability to crystallize in more than one form, a characteristic known as polymorphism, and it is understood that such polymorphic forms ("polymorphs") are within the scope of Formula I and II. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I and II or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I and II or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I and II may contain asymmetric or chiral centers, and, therefore, exist in different stereoisomeric forms. It is intended that all stereoisomeric forms of the compounds of Formula I and II, as well as mixtures thereof, including racemic mixtures, form part of the present invention. In addition, the present invention embraces all geometric and positional isomers. For example, if a compound of Formula I and II incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in Chirality in Industry (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I and II may be atropisomers (e.g. substituted biaryls) and are considered as part of this invention. Enantiomers can also be separated by use of chiral HPLC column.

It is also possible that the compounds of Formula I and II may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I and II or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I and II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and II. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and II can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I and II (e.g. those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I and II can generally be prepared by following procedures analogous to those disclosed in the Schemes and/or in the Examples hereinbelow, by substituting an appropriate isotopically labeled reagent for a non-isotopically labeled reagent.

Utility

According to another embodiment, the present invention provides a method of treating or reducing the severity of a disease in a patient by using a compound of Formulas I and II as described above, wherein said disease is selected from IRAK4 mediated pathologies, such as rheumatoid arthritis, multiple sclerosis, sepsis, osteoarthritis, inflammatory bowel disease, Parkinson's disease, cardiac contractile dysfunction, type I diabetes, type II diabetes or familial cold autoinflammatory syndrome, allergic disease, cancer, lupus, psoriasis, asthma or graft rejection.

The compounds of the invention find use in a variety of applications. As will be appreciated by those skilled in the art, the kinase activity of IRAK4 may be modulated in a variety of ways; that is, one can affect the phosphorylation/activation of IRAK4 either by modulating the initial phosphorylation of the protein or by modulating the autophosphorylation of the other active sites of the protein. Alternatively, the kinase activity of IRAK4 may be modulated by affecting the binding of a substrate of IRAK4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I and II are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg.

Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of the invention may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostate, larynx, ovaries, stomach, uterus, sarcoma and thyroid cancer; hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

The compounds of the invention may be useful for the treatment of activated B-cell-like diffuse large B-cell lymphoma (ABC-DLBCL), chronic lymphocytic leukemia (CLL) and Waldenström's Macroglobulinemia.

The instant compounds are useful in combination with a known anti-cancer agent. Combinations of the presently disclosed compounds with anti-cancer agents are within the scope of the invention. Examples of such anti-cancer agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of lupus.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of lupus.

The compounds of the instant invention are useful for the treatment of cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are: Ac (Acetyl); ACN or MeCN (acetonitrile); AcOH or HOAc (acetic acid); Boc or BOC (tert-butoxycarbonyl); Bu (butyl); Bz (benzoyl); calc'd (calculated); Cbz (benyzloxycarbonyl); CDCl$_3$ (chloroform-d); CHCl$_3$ (Chloroform); DAST ((diethylamino)sulfur trifluoride); DCM (dichloromethane); DIEA or Hinig's base (N,N-diisopropylethylamine); DMAP (4-dimethylaminopyridine); DMSO (Dimethylsulfoxide); DMF (dimethylformamide); dppf (1,1'-bis(diphenylphosphino) ferrocene); Et (ethyl); EtOH (ethanol); EtOAc (ethyl acetate); g (grams); GST (glutathione S-transferase); h (hour); HATU (N,N,N',N'-tetramethyl-O-(7-azabenzotriazol-1-yl)uronium hexafluorophosphate); HCl (hydrochloric acid); HOBt (1-hydroxybenzotriazole); HPLC (high-performance liquid chromatography); IPA or iPrOH (isopropanol); iPr (isopropyl); LC (liquid chromatography); LCMS (liquid chromatography mass spectrometry); M (molar); mCPBA (m-choroperoxybenzoic acid); Me (methyl); MeOH (methanol); mg (milligrams); min (minute); μL (microliters); mL (milliliters); mmol (millimoles); MS (mass spectrometry); MTBE (methyl tert-butyl ether); NMR (nuclear magnetic resonance spectroscopy); OAc (Acetate); Pd(dppf)Cl$_2$ (1,1'-bis(diphenylphosphino)ferrocene]dichloropalladium(II)); Ph (phenyl); POCl$_3$ (phosphorous oxychloride); Pr (propyl); rac (racemic mixture); RT or rt (room temperature (ambient, about 25° C.)); sat (saturated); SFC (supercritical fluid chromatography); tBu (tert-butyl); TEA (triethylamine (Et$_3$N)); TFA (trifluoroacetic acid); THF (tetrahydrofuran); TLC (thin layer chromatography); and Xantphos (4,5-bis (diphenylphosphino)-9,9-dimethylxanthene).

General Synopsis of Reaction Schemes

The following General Reaction Schemes, Schemes 1 to 6, provide useful details for preparing the instant compounds. The requisite intermediates are in some cases commercially available or can be prepared according to literature procedures. The illustrative General Reaction Schemes below are not limited by the compounds listed or by any particular substituents employed for illustrative purposes. Substituent labeling (i.e. R groups) as shown in the Reaction Schemes do not necessarily correlate to that used in the claims and often, for clarity, a single substituent is shown attached to the compound where multiple substituents are allowed under the definitions of Formula I hereinabove.

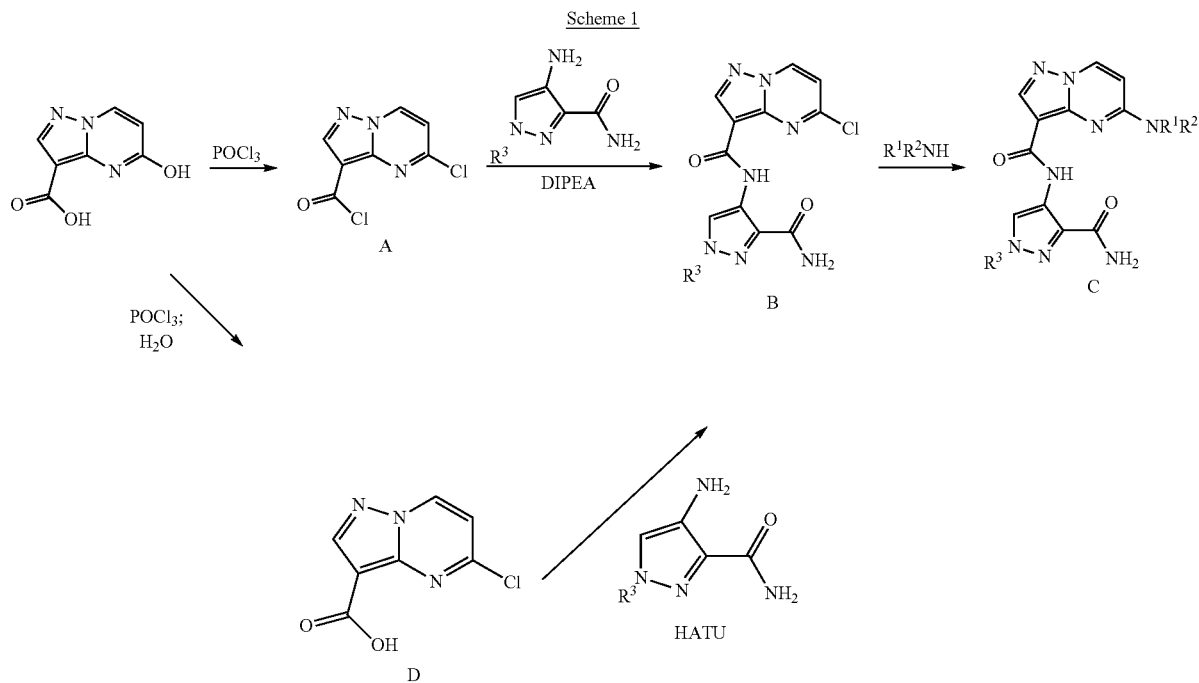

Scheme 1

Compounds of formula C are prepared via the amide formation of 5-chloropyrazolo[1,5-a]pyrimidine-3-carbonyl chloride (A) followed by S$_N$Ar reaction with an array of amines (Scheme 1). Intermediate A is prepared from 5-hydroxypyrazolo[1,5-a]pyrimidine-3-carboxylic acid by chlorination with POCl$_3$. Alternatively, 5-chloropyrazolo[1,5-a]pyrimidine-3-carboxylic acid (D) is prepared from 5-hydroxypyrazolo[1,5-a]pyrimidine-3-carboxylic acid by chlorination with POCl$_3$ and subsequent hydrolysis of the acid chloride with water. Intermediate D is then coupled with various aryl-amines in the presence of coupling reagents such as HATU to afford intermediates B.

Scheme 2

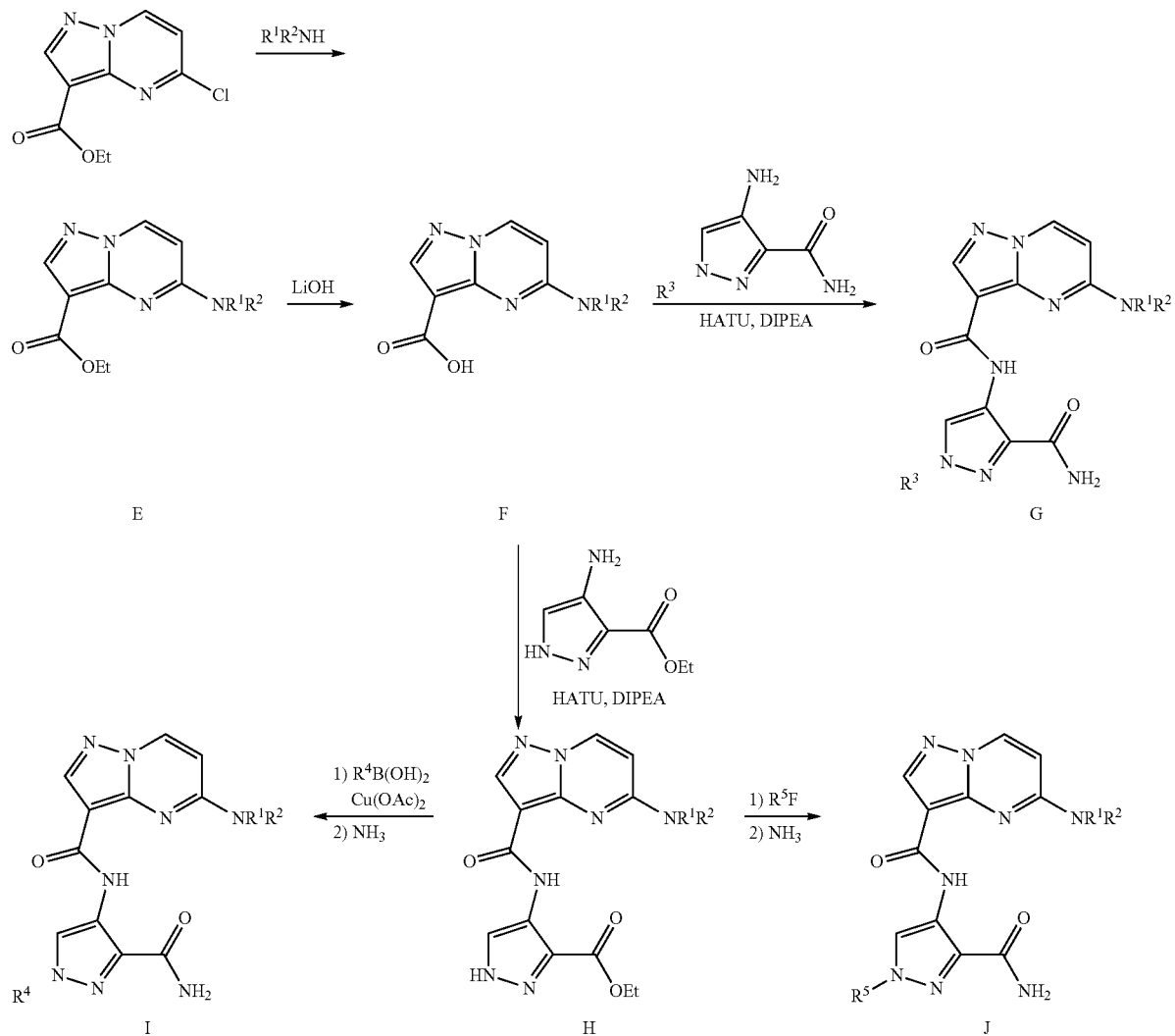

Intermediates F are prepared from ethyl 5-chloropyrazolo[1,5-a]pyrimidine-3-carboxylate via $S_NAr$ reaction followed by hydrolysis with LiOH (Scheme 2). An array of aryl-amines are coupled to carboxylic acid F employing coupling reagents such as HATU to afford compounds G. The adducts with ethyl 4-amino-1H-pyrazole-3-carboxylate (H) are further derivatized on the pyrazole via Suzuki coupling or $S_NAr$ reaction. The resultant ester intermediates are treated with $NH_3$ to afford compounds I and J.

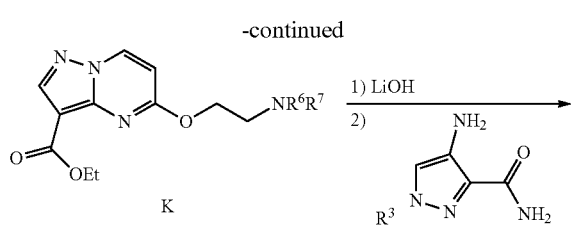

Scheme 3

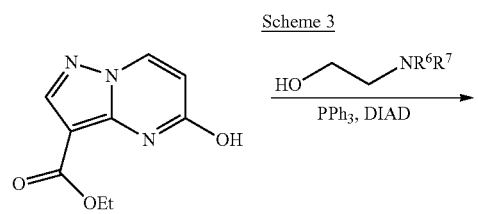

25

-continued

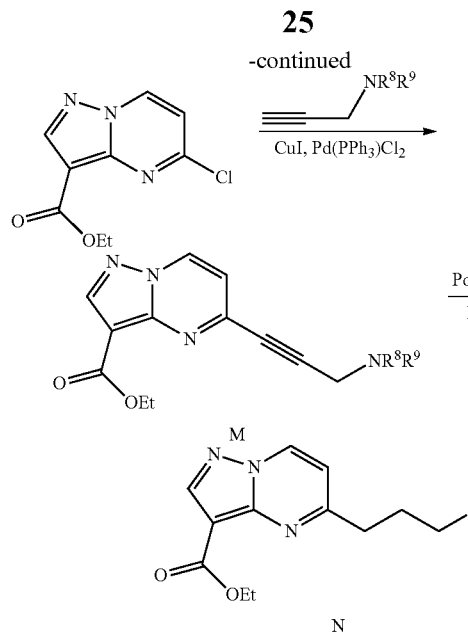

N

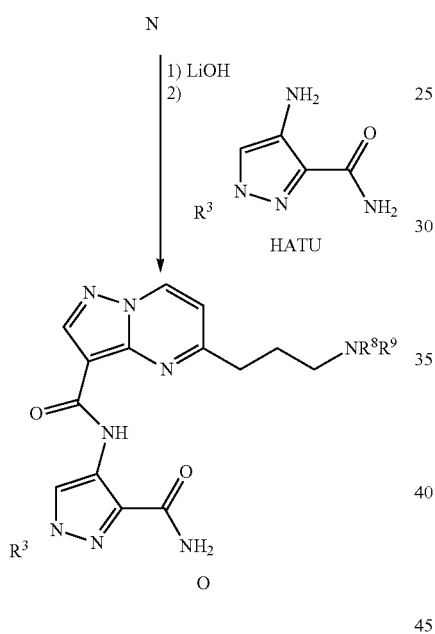

O

Intermediates K are prepared by employing Mitsunobu reaction on ethyl 5-hydroxypyrazolo [1,5-a] pyrimidine-3-carboxylate (Scheme 3). Intermediates K are converted to compounds L via sequential saponification and amide coupling. Intermediates M are prepared by employing Sonogashira coupling on ethyl 5-chloropyrazolo[1,5-a]pyrimidine-3-carboxylate. The alkynes are reduced to the corresponding alkanes by hydrogenation (H$_2$, PdOH/C) and the bicyclic core is subsequently re-oxidized with DDQ to afford intermediates N. Intermediates N are then converted to compounds O via saponification followed by amide coupling.

Scheme 4

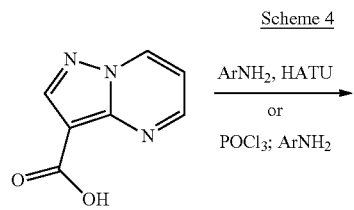

26

-continued

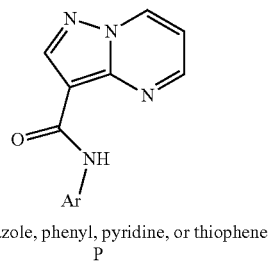

Ar = pyrazole, phenyl, pyridine, or thiophene

P

An array of aryl-amines are coupled to aryl-carboxylic acids such as pyrazolo[1,5-a]pyrimidine-3-carboxylic acid by employing coupling reagents such as HATU to afford compounds P (Scheme 4). Alternatively, aryl-carboxylic acids are converted to aryl-acid chlorides such as pyrazolo [1,5-a]pyrimidine-3-carbonyl chloride with POCl$_3$, and then coupled to aryl-amines to afford compounds P.

Scheme 5

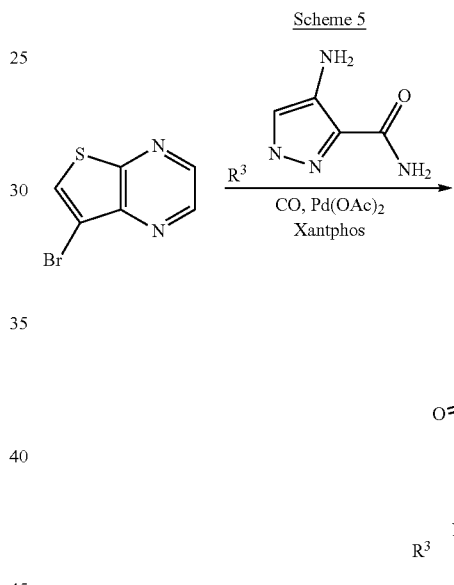

Q

Compounds Q are prepared from aryl-bromides such as 7-bromothieno[2,3-b]pyrazine by employing one-pot palladium-mediated coupling conditions in the presence of CO and aryl-amines (Scheme 5).

Scheme 6

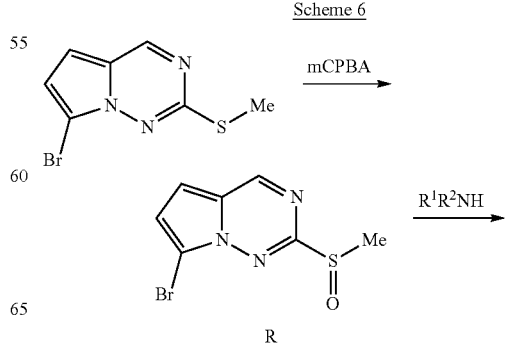

R

27
-continued

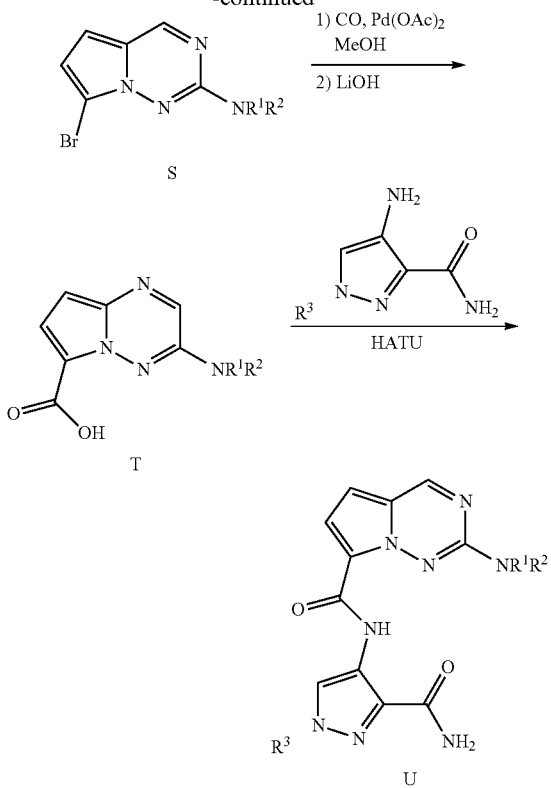

Compounds U are prepared starting from 7-bromo-2-(methylthio)pyrrolo[2,1-f][1,2,4]triazine (Scheme 6). The methylthio group is oxidized with mCPBA and the resultant sulfoxide is substituted with an array of amines to afford compounds S. Compounds S are converted to compounds U by employing sequential palladium-mediated carbonylation, saponification, and amide coupling.

Intermediate 1

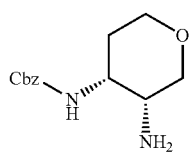

28
Benzyl ((3R,4R)-3-aminotetrahydro-2H-pyran-4-yl)carbamate

Step 1. Into a 25 mL round flask containing a solution of tert-butyl ((3R,4R)-4-aminotetrahydro-2H-pyran-3-yl)carbamate (100 mg, 0.5 mmol) in dichloromethane (5 mL) were added triethyl amine (0.15 mL, 0.9 mmol) and benzyl chloroformate (0.1 mL, 0.7 mmol) and the reaction mixture was stirred at room temperature for 2 h. The reaction mixture was diluted with dichoromethane and washed with saturated sodium bicarbonate, water, and brine solution successively. The organic fraction was dried over anhydrous sodium sulfate, filtered and concentrated under reduced pressure. The crude product was purified by flash chromatography eluting with ethyl acetate in petroleum ether (20-25%) to get benzyl tert-butyl ((3R,4R)-tetrahydro-2H-pyran-3,4-diyl)dicarbamate as a liquid. $^1$H NMR (CDCl$_3$, 400 MHz): δ 7.37-7.35 (m, 5H), 5.45 (brs, 1H), 5.12 (s, 2H), 3.94-3.81 (m, 4H), 3.59-3.53 (m, 1H), 2.01-1.96 (m, 2H), 1.45 (s, 9H). MS calc'd [M-Boc+H]$^+$251.2, found 251.2.

Step 2. Into a 10 mL round bottom flask containing a solution benzyl tert-butyl ((3R,4R)-tetrahydro-2H-pyran-3,4-diyl)dicarbamate (130 mg, 0.4 mmol) in anhydrous 1,4-dioxane (1 mL) was added hydrochloric acid (4.4 M in dioxane, 1 mL) and stirred for 2 h at room temperature. The solvent was removed under reduced pressure and the residue was purified by flash chromatography eluting with methanol in dichloromethane (4-7%) to yield benzyl ((3R,4R)-3-aminotetrahydro-2H-pyran-4-yl)carbamate as a solid. $^1$H NMR (CDCl$_3$, 300 MHz): δ 7.37-7.29 (m, 5H), 5.17 (s, 2H), 4.37-4.32 (m, 1H), 4.01-3.89 (m, 2H), 3.77-3.53 (m, 2H), 3.41-3.38 (m, 1H), 1.85-1.67 (m, 2H). MS calc'd [M+H]$^+$ 251.1, found 251.2.

The following intermediate was prepared in an analogous manner of that described in Intermediate 1.

| Intermediate # | Structure | IUPAC Name | Exact Mass [M + H]$^+$ |
|---|---|---|---|
| 2 | ![structure] | benzyl ((3S,4S)-4-amino-1,1-dioxidotetrahydro-2H-thiopyran-3-yl)carbamate | Calc'd 299.1, found 299.2. |

Intermediate 3

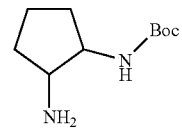

tert-Butyl N-(2-aminocyclopentyl)carbamate

Step 1. Into a 50 mL round-bottom flask purged and maintained with an inert atmosphere of nitrogen was placed a solution of 2-aminocyclopentan-1-ol (1.0 g, 9.9 mmol) and TEA (4.0 g, 40 mmol) in dichloromethane (25 mL). The resulting solution was stirred for 5 min at 0° C. This was followed by the addition of di-tert-butyl dicarbonate (2374.4 mg, 10.88 mmol) dropwise with stirring at 0° C. The resulting solution was allowed to stir for an additional 5 h at 25° C., then washed with 2×100 mL of water, dried over $Na_2SO_4$, filtered and concentrated under reduced pressure. This resulted in tert-butyl N-(2-hydroxycyclopentyl)carbamate as a solid. MS $[M+H]^+$202.

Step 2. Into a 50 mL round-bottom flask purged and maintained with an inert atmosphere of nitrogen was placed a solution of tert-butyl N-(2-hydroxycyclopentyl)carbamate (860 mg, 4.28 mmol) and TEA (1300 mg, 12.8 mmol) in dichloromethane (9 mL). This was followed by the addition of methanesulfonyl chloride (735 mg, 6.41 mmol) dropwise with stirring at 0° C. The resulting solution was stirred for 3 h at 0° C., washed with 1×100 mL of sodium bicarbonate, dried over $Na_2SO_4$, filtered and concentrated under reduced pressure. This resulted in tert-butyl N-[2-(methanesulfonyloxy)cyclopentyl]carbamate as an oil. MS $[M+H]^+$ 280.

Step 3. Into a 20 mL pressure tank reactor was placed a solution of tert-butyl N-[2-(methanesulfonyloxy)cyclopentyl]carbamate (300 mg, 1.07 mmol) in $NH_4OH$ (6 mL). The resulting solution was stirred overnight at 50° C. in an oil bath. The resulting solution was concentrated under reduced pressure. This resulted in tert-butyl N-(2-aminocyclopentyl)carbamate as an oil. MS $[M+H]^+$ 201.

Intermediate 4

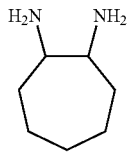

Cycloheptane-1,2-diamine

Into a 25 mL round-bottom flask purged and maintained with an inert atmosphere of nitrogen were placed lithium aluminium hydride (389 mg, 10.2 mmol) and tetrahydrofuran (5 mL). This was followed by the addition of a solution of N-[(1E,2E)-2-(hydroxyimino)cycloheptylidene] hydroxylamine (200 mg, 1.28 mmol) in tetrahydrofuran (5 mL) dropwise with stirring. The resulting solution was stirred for 16 h at 50° C. in an oil bath. The reaction was then treated with 3 g of sodium sulfate decahydrate and diluted with 30 mL of diethyl ether. The solids were filtered out. The resulting solution was concentrated under vacuum. This resulted in cycloheptane-1,2-diamine as an oil. MS $[M+H]^+$ 129.

Intermediate 5

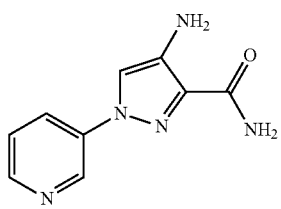 [SMILES: NC(=O)c1nn(-c2cccnc2)cc1N]

4-Amino-1-(pyridin-3-yl)-1H-pyrazole-3-carboxamide

Step 1. Into a 1 L round-bottom flask were placed ethyl 4-nitro-1H-pyrazole-3-carboxylate (15 g, 81 mmol), (pyridin-3-yl)boronic acid (10 g, 81 mmol) and copper(II) acetate (15 g, 83 mmol) in N,N-dimethylformamide (400 mL). This was followed by the addition of pyridine (6.4 g, 81 mmol) dropwise with stirring at room temperature. The resulting solution was stirred for 5 h at 80° C. in an oil bath, then concentrated under vacuum. The residue was purified by flash chromatography on silica gel, eluting with a mixture of 5% MeOH in $CH_2Cl_2$. This resulted in ethyl 4-nitro-1-(pyridin-3-yl)-1H-pyrazole-3-carboxylate as an oil. MS $[M+H]^+$ 263.

Step 2. Into a 100 mL round-bottom flask was placed a slurry of ethyl 4-nitro-1-(pyridin-3-yl)-1H-pyrazole-3-carboxylate (3 g, 11.44 mmol) and palladium on carbon (0.5 g) in tetrahydrofuran (30 mL). The resulting slurry was stirred for 12 h at room temperature under an atmosphere of hydrogen. The solids were filtered out. The resulting mixture was concentrated under reduced pressure. This resulted in ethyl 4-amino-1-(pyridin-3-yl)-1H-pyrazole-3-carboxylate as a solid. MS $[M+H]^+$ 233.

Step 3. Into a 50 mL sealed tube were placed ethyl 4-amino-1-(pyridin-3-yl)-1H-pyrazole-3-carboxylate (1 g, 4.31 mmol) and ammonia water (10 mL). The resulting solution was stirred for 12 h at 95° C. in an oil bath. After removal of the solvent, the residue was purified by flash chromatography on silica gel, eluting with a mixture of 5% MeOH in $CH_2Cl_2$. This resulted in 4-amino-1-(pyridin-3-yl)-1H-pyrazole-3-carboxamide as a solid. $^1$H NMR (400 MHz, DMSO-$d_6$): δ 4.94 (m, 2H), 7.31 (s, 1H), 7.51-7.59 (m, 2H), 7.88 (s, 1H), 8.21-8.23 (m, 1H), 8.49-8.50 (m, 1H), 9.13 (d, J=2.0 Hz, 1H). MS $[M+H]^+$ 204.

Intermediate 6

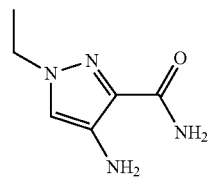

4-Amino-1-ethyl-1H-pyrazole-3-carboxamide

Step 1. Into a 50 mL round bottom flask containing a solution of 4-nitro-1H-pyrrazole-3-carboxalic acid (5.0 g, 32 mmol) in methanol (50 mL) was added concentrated sulfuric acid (1 mL) at 0° C. The resulting slurry was stirred at reflux temperature overnight. The solvents were evaporated under reduced pressure and the residual mass was dissolved in ethyl acetate and washed with water and brine solution. The organic layer was dried over anhydrous sodium sulfate, filtered and concentrated to yield methyl 4-nitro-1H-pyrazole-3-carboxylate as a solid which was taken to next step without further purification. $^1$H NMR (CD$_3$OD, 300 MHz): δ 8.59 (s, 1H), 3.93 (s, 3H). MS calc'd $[M-H]^+$170.0, found 170.1.

Step 2. A solution of methyl 4-nitro-1H-pyrazole-3-carboxylate (5.0 g, 29 mmol) in aqueous ammonia solution (50 mL) in a 100 mL sealed tube was stirred at 90° C. overnight. The solvents were evaporated under reduced pressure to give 4-nitro-1H-pyrazole-3-carboxamide as a solid. $^1$H NMR (DMSO-$d_6$, 300 MHz): δ 8.71 (s, 1H), 8.06 (s, 1H), 7.83 (s, 1H). MS calc'd [M+H] 157.0, found 157.2.

Step 3. Into a 50 mL round bottom flask containing a solution of 4-nitro-1H-pyrazole-3-carboxamide (307 mg, 1.96 mmol) in dimethylformamide (5 mL) were added potassium carbonate (543 mg, 3.9 mmol) and iodoethane (366 mg, 2.36 mmol). The reaction mixture was stirred at room temperature overnight. The reaction mixture was extracted with ethyl acetate and the combined organics were washed with water and brine, dried over sodium sulfate, filtered and concentrated. The crude was purified over silica gel column chromatography eluting with methanol in dichloromethane (4-6%) to afford 1-ethyl-4-nitro-1H-pyrazole-3-carboxamide as a solid. $^1$H NMR (DMSO-$d_6$, 400 MHz): δ 8.89 (s, 1H), 8.01 (s, 1H), 7.76 (s, 1H), 4.19 (q, J=7.3 Hz, 2H), 1.41 (t, J=7.3 Hz, 3H). MS calc'd [M+H]+ 185.1, found 185.2.

Step 4. Into a 25 mL round bottom flask containing a solution of 1-ethyl-4-nitro-1H-pyrazole-3-carboxamide (70 mg, 0.38 mmol) in methanol (5 mL) was added palladium on carbon (15 mg, 20% w/w) and the reaction mixture was stirred at room temperature for 4 h under hydrogen bladder pressure. The reaction mixture was filtered through celite and washed with methanol and the filtrate was concentrated under reduced pressure. The residue was purified by flash chromatography eluting with methanol in dichloromethane (5-7%) to yield 4-amino-1-ethyl-1H-pyrazole-3-carboxamide as a solid. $^1$H NMR (DMSO-$d_6$, 400 MHz): δ 7.10-7.07 (m, 2H), 6.94 (s, 1H), 4.61 (s, 2H), 4.02-3.96 (m, 2H), 1.34-1.30 (m, 3H). MS calc'd [M−H]+ 155.1, found 155.2.

The following intermediates were prepared in an analogous manner of that described in Intermediate 6.

Intermediate 10

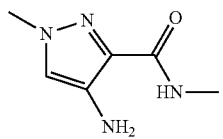

4-Amino-N,1-dimethyl-1H-pyrazole-3-carboxamide

Step 1. Into a 100 mL round bottom flask containing a solution of methyl 4-nitro-1H-pyrazole-3-carboxylate (3.0 g, 17.5 mmol) in dimethylformamide (25 mL) were added potassium carbonate (4.8 g, 35 mmol) and iodomethane (2.2 mL, 35 mmol) and the reaction mixture was stirred at room temperature for 2 h. The reaction mixture was diluted with ethyl acetate, washed with water and brine solution, dried over anhydrous sodium sulfate, filtered and concentrated under reduced pressure. The crude was purified by flash chromatography eluting with ethyl acetate in petroleum ether (35-50%) to afford methyl 1-methyl-4-nitro-1H-pyrazole-3-carboxylate as a solid. $^1$H NMR (CDCl$_3$, 400 MHz): δ 8.16 (s, 1H), 4.02 (s, 3H), 4.01 (s, 3H). MS calc'd [M+H]$^+$ 186.0, found 186.2.

Step 2. A mixture of methyl 1-methyl-4-nitro-1H-pyrazole-3-carboxylate (1.7 g, 9 mmol) and methyl amine (40% in water, 50 mL) in a 100 mL sealed tube was stirred at 90° C. overnight. The solvents were evaporated under reduced pressure to give N, 1-dimethyl-4-nitro-1H-pyrazole-3-carboxamide (1.7 g) as white solid. The product obtained was taken to next step without further purification. $^1$H NMR (DMSO-$d_6$, 400 MHz): δ 8.81 (s, 1H), 7.99 (s, 1H), 3.87 (s, 3H), 3.75 (s, 3H). MS calc'd [M+H]$^+$ 185.1, found 185.2.

Step 3. Into a 100 mL round bottom flask containing a solution of N, 1-dimethyl-4-nitro-1H-pyrazole-3-carboxam-

| Intermediate # | Structure | IUPAC Name | Exact Mass [M + H]+ |
|---|---|---|---|
| 7 | ![structure] | 4-amino-1-isopropyl-1H-pyrazole-3-carboxamide | Calc'd 169.1, found 169.2. |
| 8 | ![structure] | 4-amino-1-(2-methoxyethyl)-1H-pyrazole-3-carboxamide | Calc'd 185.1, found 185.2. |
| 9 | ![structure] | 4-amino-1-(2-((tert-butyldimethylsilyl)oxy)ethyl)-1H-pyrazole-3-carboxamide | Calc'd 285.2, found 285.2. | ide (1.7 g, 9.2 mmol) in methanol (30 mL) was added palladium on carbon (170 mg, 10% w/w) and stirred at room temperature overnight under hydrogen bladder pressure. The reaction mixture was filtered through celite and washed with methanol and the filtrate was concentrated under reduced pressure. The residue was purified by flash chromatography eluting with methanol in dichloromethane (5-7%) to yield 4-amino-N,1-dimethyl-1H-pyrazole-3-carboxamide as a solid. $^1$H NMR (DMSO-d$_6$, 400 MHz): δ 7.73 (brs, 1H), 7.07 (s, 1H), 4.62 (s, 2H), 3.73 (s, 3H), 2.69 (s, 3H). MS calc'd [M+H]$^+$ 155.1, found 155.2.

The following intermediates were prepared in an analogous manner of that described in Intermediate 10.

solution. The organic fraction was dried over anhydrous sodium sulfate, filtered and concentrated under reduced pressure. The residue was purified by flash chromatography eluting with methanol in dichloromethane (2-5%) to afford methyl 1-methylpiperidine-3-carboxylate as a liquid. MS calc'd [M+H]$^+$ 158.1, found 158.2.

Step 3. Into a 500 mL round bottom flask containing a solution of methyl 1-methylpiperidine-3-carboxylate (12.0 g, 76 mmol) in tetrahydrofuran (500 mL) was added lithium aluminumhydride (4.3 g, 114 mmol) in portions at 0° C. and the reaction mixture was stirred at room temperature for 1 h. The reaction was quenched with methanol at 0° C. and the precipitated solid was filtered through celite. The filtrate was

| Intermediate # | Structure | IUPAC Name | Exact Mass [M + H]$^+$ |
|---|---|---|---|
| 11 | 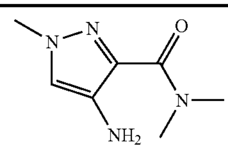 | 4-amino-N,N,1-trimethyl-1H-pyrazole-3-carboxamide | Calc'd 169, found 169 |
| 12 | 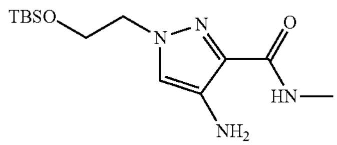 [SMILES: CNC(=O)c1nn(CCO[Si](C)(C)C(C)(C)C)cc1N] | 4-amino-1-(2-((tert-butyldimethylsilyl)oxy)ethyl)-N-methyl-1H-pyrazole-3-carboxamide | Calc'd 299.2, found 299.3 |

Intermediate 13

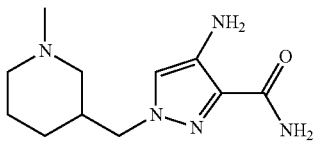 [SMILES: CN1CCCC(Cn2cc(N)c(C(N)=O)n2)C1]

4-Amino-1-((1-methylpiperidin-3-yl)methyl)-1H-pyrazole-3-carboxamide

Step 1. Into a 500 mL round bottom flask containing a solution of piperidine-3-carboxylic acid (15.0 g, 116 mmol) in methanol (150 mL) was added conc. H$_2$SO$_4$ at 0° C. and the reaction mixture was heated at 80° C. overnight. The solvent was removed under reduced pressure and the crude was dissolved in ethyl acetate (500 mL) and washed with water and brine solution. The organic fraction was dried over anhydrous sodium sulfate, filtered and concentrated under reduced pressure to afford methyl piperidine-3-carboxylate as a solid. $^1$H NMR (DMSO-d$_6$, 300 MHz): δ 3.64 (s, 3H), 3.35 (brs, 1H), 3.17-3.12 (m, 1H), 2.97-2.92 (m, 1H), 2.77-2.71 (m, 2H), 1.97-1.95 (m, 1H), 1.76-1.74 (m, 1H), 1.60-1.56 (m, 2H). MS calc'd [M+H]$^+$ 144.1, found 144.2.

Step 2. Into a 1000 mL round bottom flask containing a solution of methyl piperidine-3-carboxylate (16 g, 110 mmol) in methanol (200 mL) was added formaldehyde solution (38% in water, 26 mL, 216 mmol) at 0° C. and stirred for 15 min. To this reaction mixture was added sodium cyanoborohydride (13.5 g, 216 mmol) and stirred overnight at room temperature. The solvent was evaporated under reduced pressure and the residue was dissolved in ethyl acetate (500 mL) and washed with water and brine concentrated and the crude was purified by flash chromatography eluting with methanol in dichloromethane (5-10%) to afford (1-methylpiperidin-3-yl)methanol as a solid. $^1$H NMR (DMSO-d$_6$, 400 MHz): δ 3.38-3.35 (m, 1H), 3.27-3.20 (m, 1H), 3.18-3.15 (m, 1H), 2.77-2.72 (m, 1H), 2.66-2.60 (m, 2H), 2.10 (s, 3H), 1.78-1.75 (m, 1H), 1.73-1.51 (m, 4H), 1.48-1.29 (m, 1H). MS calc'd [M+H]$^+$ 130.1, found 130.2.

Step 4. Into a 250 mL round bottom flask containing a solution of (1-methylpiperidin-3-yl)methanol (8.0 g, 62 mmol) in dichloromethane (80 mL) was added triethylamine (17 mL, 125 mmol) followed by the addition of p-toluenesulfonyl chloride (14.2 g, 75 mmol) and the reaction mixture stirred at room temperature for 5 h. The reaction mixture was diluted with dichloromethane and washed with water and brine solution. The organic fraction was dried over anhydrous sodium sulfate, filtered and concentrated under reduced pressure. The crude was purified by flash chromatography eluting with methanol in dichloromethane (5-7%) to afford (1-methylpiperidin-3-yl)methyl 4-methylbenzenesulfonate as a liquid. $^1$H NMR (DMSO-d$_6$, 400 MHz): δ 7.80 (d, J=7.8 Hz, 2H), 7.11 (d, J=7.8 Hz, 2H), 4.01-3.91 (m, 2H), 3.21-3.16 (m, 2H), 2.64-2.58 (m, 2H), 2.43 (s, 3H), 2.42-2.29 (m, 1H), 2.09 (s, 3H), 1.77-1.74 (m, 2H), 1.62-1.59 (m, 2H). MS calc'd [M+H]$^+$ 284.1, found 284.4.

Step 5. Into a 250 mL round flask containing a solution of (1-methylpiperidin-3-yl)methyl 4-methylbenzenesulfonate (7.5 g, 27 mmol) in acetone (120 mL) was added sodium iodide (30.0 g, 198 mmol) and the reaction mixture refluxed at 90° C. for 1 h. The filtrate was concentrated and the crude was purified by flash chromatography eluting with methanol in dichloromethane (5-10%) to afford 3-(iodomethyl)-1-methylpiperidine as a liquid. MS calc'd [M+H]$^+$ 240.0, found 240.2.

Step 6. Into a 100 mL round bottom flask containing a solution of 4-nitro 1H-pyrrazole methyl 3-carboxylate (1.0 g, 5.5 mmol) in dimethylformamide (10 mL) was added a solution 3-(iodomethyl)-1-methylpiperidine (2.6 g, 11 mmol) in dimethylformamide (2 mL) followed by the addition of potassium carbonate (1.5 g 11 mmol) and the reaction mixture was stirred at room temperature overnight. The solvent was removed under reduced pressure and the crude was dissolved in ethyl acetate and washed with water and brine solution. The organic fraction was dried over anhydrous sodium sulfate, filtered, and concentrated under reduced pressure. The crude mixture was purified by flash chromatography eluting with methanol in dichloromethane (5-10%) to afford methyl 1-((1-methylpiperidin-3-yl)methyl)-4-nitro-1H-pyrazole-3-carboxylate as a solid. $^1$H NMR (DMSO-$d_6$, 400 MHz): δ 9.01 (s, 1H), 4.16 (d, J=6.8 Hz, 2H), 3.98 (s, 3H), 3.40-3.36 (m, 2H), 3.28-3.21 (m, 2H), 2.84-2.81 (m, 1H), 2.48 (s, 3H), 1.84-1.78 (m, 2H), 1.67-1.65 (m, 2H). MS calc'd [M+H]$^+$ 283.1, found 283.2.

Step 7. A mixture of methyl 1-((1-methylpiperidin-3-yl)methyl)-4-nitro-1H-pyrazole-3-carboxylate (400 mg, 1.4 mmol) and aqueous ammonia (30% in water, 20 mL) in a 100 mL sealed tube was heated at 90° C. overnight. The solvent was removed under reduced pressure to afford 1-((1-methylpiperidin-3-yl)methyl)-4-nitro-1H-pyrazole-3-carboxamide as a solid. $^1$H NMR (DMSO-$d_6$, 300 MHz): δ 8.86 (s. 1H), 7.97 (brs, 1H), 7.74 (brs, 1H), 4.07 (d, J=6.6 Hz, 2H), 3.42-3.39 (m, 2H), 3.24-3.2 (m, 2H), 2.51-2.48 (m, 1H), 1.74-1.71 (m, 2H), 1.50-1.48 (m, 2H).

Step 8. Into a 50 mL round bottom flask containing a solution of 1-((1-methylpiperidin-3-yl)methyl)-4-nitro-1H-pyrazole-3-carboxamide (150 mg, 0.6 mmol) in methanol (5 mL) was added palladium on carbon (15 mg, 10% w/w) and stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 4-amino-1-((1-methylpiperidin-3-yl)methyl)-1H-pyrazole-3-carboxamide as a solid. MS calc'd [M+H]$^+$238.2, found 238.0.

Intermediate 14

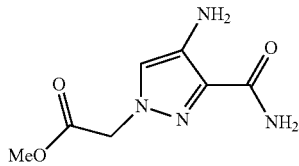 [SMILES: COC(=O)Cn1cc(N)c(C(N)=O)n1]

Methyl 2-(4-amino-3-carbamoyl-1H-pyrazol-1-yl)acetate

Step 1. Into a 25 mL round flask containing a solution of 4-nitro-1H-pyrazole-3-carboxamide (500 mg, 3.2 mmol) in dimethylformamide (5 mL) were added potassium carbonate (900 mg, 6.5 mmol) and ethyl bromoacetate (0.6 mL, 5 mmol) and the reaction mixture was stirred at room temperature for 16 h. The reaction mixture was pored into water and extracted with ethyl acetate. The organic fraction was washed with water and brine solution and dried over anhydrous sodium sulfate, filtered and concentrated under reduced pressure. The crude product was purified by flash chromatography eluting with ethyl acetate in petroleum ether (50-70%) to get ethyl 2-(3-carbamoyl-4-nitro-1H-pyrazol-1-yl)acetate. $^1$H NMR (DMSO-$d_6$, 400 MHz): δ 8.86 (s, 1H), 8.04 (s, 1H), 7.79 (brs, 1H), 5.17 (s, 2H), 4.19 (q, J=7.1 Hz, 2H), 1.22 (t, J=7.1 Hz, 3H). MS calc'd [M+H]$^+$ 243.1, found 243.0.

Step 2. Into a 50 mL round bottom flask containing a solution of ethyl 2-(3-carbamoyl-4-nitro-1H-pyrazol-1-yl)acetate (300 mg, 1.2 mmol) in methanol (20 mL) was added palladium on carbon (30 mg, 10% w/w) and stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (3-5%) to afford methyl 2-(4-amino-3-carbamoyl-1H-pyrazol-1-yl)acetate as a solid. MS calc'd [M+H]$^+$ 199.1, found 199.0.

Intermediate 15

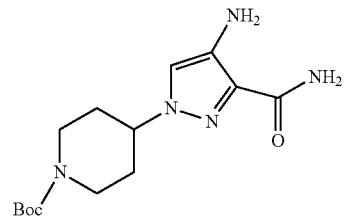 [SMILES: CC(C)(C)OC(=O)N1CCC(n2cc(N)c(C(N)=O)n2)CC1]

tert-Butyl 4-(4-amino-3-carbamoyl-1H-pyrazol-1-yl)piperidine-1-carboxylate

Step 1. Into a 500 mL round-bottom flask were placed tert-butyl 4-hydroxypiperidine-1-carboxylate (10 g, 49.69 mmol) and triethylamine (7.54 g, 74.51 mmol) in dichloromethane (200 mL). This was followed by the addition of methanesulfonyl chloride (6.88 g, 60.1 mmol) dropwise with stirring at 0° C. The resulting solution was stirred for 3 h at 25° C. After removal of the solvent, the residue was purified by flash chromatography on a silica gel column, eluting with dichloromethane/methanol (100:1-5:1). This resulted in tert-butyl 4-(methanesulfonyloxy) piperidine-1-carboxylate as a solid. MS [M+H]$^+$ 280.

Step 2. Into a 25 mL round-bottom flask were placed tert-butyl 4-(methanesulfonyloxy) piperidine-1-carboxylate (1 g, 3.58 mmol) in N,N-dimethylformamide (10 mL), 4-nitro-1H-pyrazole-3-carboxamide (671 mg, 4.30 mmol), and cesium carbonate (3.51 g, 10.8 mmol). The resulting solution was stirred for 3 h at 100° C. The reaction mixture was cooled to room temperature. After removal of the solvent, the residue was purified by flash chromatography on a silica gel column, eluting with dichloromethane/methanol (100:1-10:1). This resulted in tert-butyl 4-(3-carbamoyl-4-nitro-1H-pyrazol-1-yl) piperidine-1-carboxylate as a crystal. MS [M+H]$^+$ 340.

Step 3. Into a 50 mL round-bottom flask purged and maintained with an inert atmosphere of hydrogen was placed a solution of tert-butyl 4-(3-carbamoyl-4-nitro-1H-pyrazol-1-yl) piperidine-1-carboxylate (960 mg, 2.83 mmol) in methanol (20 mL), and then palladium on carbon (0.2 g) was added. The resulting solution was stirred for 1.5 h at room temperature. The solids were filtered out. The resulting solution was concentrated under reduced pressure. This resulted in tert-butyl 4-(4-amino-3-carbamoyl-1H-pyrazol-1-yl) piperidine-1-carboxylate as a solid. MS [M+H]+ 310.

The following intermediates were prepared in an analogous manner of that described in Intermediate 15.

| Intermediate # | Structure | IUPAC Name | Exact Mass [M + H]+ |
| --- | --- | --- | --- |
| 16 | 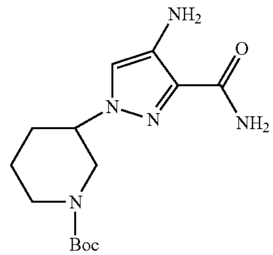 [SMILES: CC(C)(C)OC(=O)N1CCCC(n2cc(N)c(C(N)=O)n2)C1] | tert-butyl 3-(4-amino-3-carbamoyl-1H-pyrazol-1-yl)piperidine-1-carboxylate | Calc'd 310, found 310. |
| 17 | 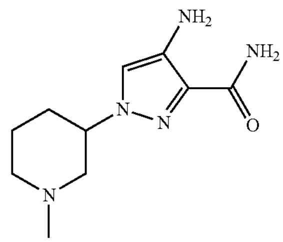 [SMILES: CN1CCCC(n2cc(N)c(C(N)=O)n2)C1] | 4-amino-1-(1-methylpiperidin-3-yl)-1H-pyrazole-3-carboxamide | Calc'd 224, found 224. |

Example 1

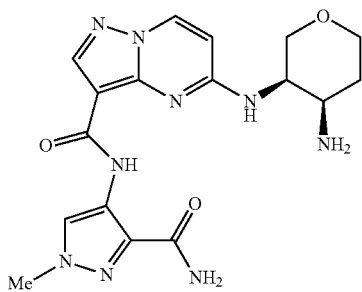 [SMILES: Cn1cc(NC(=O)c2cnn3ccc(N[C@H]4COCC[C@H]4N)nc23)c(C(N)=O)n1]

5-(((3R,4R)-4-Aminotetrahydro-2H-pyran-3-yl)amino)-N-(3-carbamoyl-1-methyl-1H-pyrazol-4-yl)pyrazolo[1,5-a]pyrimidine-3-carboxamide (IRAK4 IC$_{50}$=31 nM)

Step 1. Into a 100 mL sealed tube were added 5-hydroxypyrazolo[1,5-a]pyrimidine-3-carboxylic acid (3.0 g, 17 mmol), phosphorous oxychloride (30 mL) and diisopropylethylamine (3 mL) and the resulting solution was stirred at 120° C. for 8 h. The reaction mixture was cooled to room temperature and concentrated under reduced pressure. The residue thus obtained was dissolved in dichloromethane (15 mL) and concentrated to remove any residual amount of phosphorous oxychloride which afforded 5-chloropyrazolo[1,5-a]pyrimidine-3-carbonyl chloride which was taken to next step without further purification.

Step 2. Into a 100 mL round bottomed flask were added 5-chloropyrazolo[1,5-a]pyrimidine-3-carbonyl chloride, dichloromethane (20 mL), 4-amino-1-methyl-1H-pyrazole-3-carboxamide (2.3 g, 17 mmol) and diisopropylethylamine (5.7 mL 34 mmol) and the reaction mixture was stirred at room temperature for 1 h. The reaction mixture was diluted with dichloromethane, washed with water and brine solution, dried over anhydrous sodium sulfate, filtered and concentrated. The crude product was purified by flash chromatography eluting with methanol in dichloromethane (1-4%) to afford N-(3-carbamoyl-1-methyl-1H-pyrazol-4-yl)-5-chloropyrazolo[1,5-a]pyrimidine-3-carboxamide as a solid. $^1$H NMR (DMSO-d$_6$ 400 MHz): δ 10.97 (s, 1H), 9.35 (d, J=7.2 Hz, 1H), 8.69 (s, 1H), 8.38 (s, 1H), 7.55 (s, 1H), 7.48 (s, 1H), 7.39 (d, J=7.2 Hz, 1H), 3.91 (s, 3H). MS calc'd [M+H]+ 320.1, found 320.3.

Step 3. Into a 10 mL round bottomed flask containing a solution of 5-chloro-N-(1-(pyridin-3-yl)-1H-pyrazol-4-yl)pyrazolo[1,5-a]pyrimidine-3-carboxamide (102 mg, 0.32 mmol) in dimethyl sulfoxide (2 mL) were added potassium fluoride (56 mg, 0.96 mmol) and benzyl (3R,4R)-3-aminotetrahydro-2H-pyran-4-yl)carbamate (80 mg, 0.32 mmol) and the mixture was stirred at 80° C. for 2 h. The reaction mixture was diluted with ethyl acetate (50 mL) and washed with water (15 mL×3) and brine, and the combined organics were dried over sodium sulfate and concentrated. The residue thus obtained was purified by flash chromatography eluting with methanol in dichloromethane (3-5%) to afford of benzyl ((3R,4R)-3-((3-((3-carbamoyl-1-methyl-1H-pyrazol-4-yl)carbamoyl)pyrazolo[1,5-a]pyrimidin-5-yl)amino)tetrahydro-2H-pyran-4-yl)carbamate as a solid. $^1$H NMR (CD$_3$OD, 400 MHz): δ 10.85 (s, 1H), 8.33 (d, J=6.4 Hz, 1H), 8.25-8.24 (m, 2H), 7.17 (brs, 3H), 7.05 (brs, 2H), 6.54 (d, J=6.8 Hz, 1H), 5.52 (brs, 1H), 4.88-4.78 (m, 1H), 4.11-3.94 (m, 4H), 3.92 (s, 2H), 2.66 (s, 3H), 1.97-1.75 (m, 1H), 1.74-1.73 (m, 1H). MS calc'd [M+H]+ 534.2, found 534.4.

Step 4. Into a 25 mL round bottom flask containing a solution of benzyl ((3R,4R)-3-((3-((3-carbamoyl-1-methyl-1H-pyrazol-4-yl)carbamoyl)pyrazolo[1,5-a]pyrimidin-5-yl)amino)tetrahydro-2H-pyran-4-yl)carbamate (70 mg, 0.13 mmol) in methanol (5 mL) was added palladium on carbon (10 mg, 15% w/w) and stirred at room temperature for 16 h under hydrogen bladder pressure. The reaction mixture was filtered through celite and washed with methanol and the filtrate was concentrated under reduced pressure. The residue was purified by preparative HPLC to yield 5-(((3R,4R)-4-aminotetrahydro-2H-pyran-3-yl)amino)-N-(3-carbamoyl-1-methyl-1H-pyrazol-4-yl)pyrazolo[1,5-a]pyrimidine-3-carboxamide trifluoroacetate. $^1$H NMR (CD$_3$OD, 400 MHz): δ 10.73 (s, 1H), 8.46 (d, J=7.6 Hz, 1H), 8.32 (s, 1H), 8.29 (t, J=1.8 Hz, 1H), 6.69 (d, J=7.6 Hz, 1H), 5.24-5.22 (m, 1H), 4.18-4.14 (m, 1H), 4.09-4.01 (m, 2H), 3.96 (s, 3H), 3.79-3.76 (m, 1H), 3.67-3.61 (m, 1H), 2.17-2.03 (m, 1H), 1.92-1.89 (m, 1H). MS calc'd [M+H]$^+$ 400.2, found 400.4.

N-(3-Carbamoyl-1-methyl-1H-pyrazol-4-yl)-5-chloropyrazolo[1,5-a]pyrimidine-3-carboxamide was also prepared in 2 steps as described below.

Step 1. Into a 25 mL round-bottom flask were placed 5-hydroxypyrazolo[1,5-a]pyrimidine-3-carboxylic acid (220 mg, 1.23 mmol) and POCl$_3$ (10 mL). This was followed by the addition of DIPEA (0.6 mL) dropwise with stirring at 0° C. The resulting solution was stirred for 3 h at 80° C. The resulting mixture was concentrated under reduced pressure. The resulting solution was diluted with 10 mL of water and stirred for 30 min. The solids were collected by filtration. The solid was dried in an oven under reduced pressure. This resulted in 5-chloropyrazolo[1,5-a]pyrimidine-3-carboxylic acid as a solid.

Step 2. Into a 50 mL round-bottom flask were placed 5-chloropyrazolo[1,5-a]pyrimidine-3-carboxylic acid (200 mg, 1.01 mmol), 4-amino-1-methyl-1H-pyrazole-3-carboxamide (95 mg, 0.68 mmol), HATU (385 mg, 1.01 mmol), DIPEA (174 mg), and MeCN (30 mL). The resulting solution was stirred for 10 h at 60° C. in an oil bath. After concentrated under reduced pressure, the residue was dissolved with 50 mL of DCM, washed with 2×30 mL of water. The organic phase was concentrated to 10 mL and the product was precipitated and collected by filtration to give N-(3-carbamoyl-1-methyl-1H-pyrazol-4-yl)-5-chloropyrazolo[1,5-a]pyrimidine-3-carboxamide as a solid.

The following examples were prepared in an analogous manner of that described in Example 1.

| Example # | IRAK4 IC$_{50}$ (nM) | Structure | IUPAC Name | Exact Mass [M + H]$^+$ |
|---|---|---|---|---|
| 2 | 0.6 | 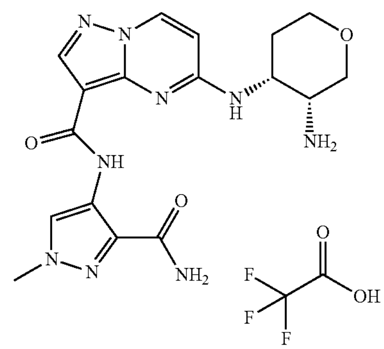 [SMILES: Cn1cc(NC(=O)c2cnn3ccc(N[C@@H]4CCOC[C@@H]4N)nc23)c(C(N)=O)n1 ; O=C(O)C(F)(F)F] | 5-{[(3R,4R)-3-aminotetrahydro-2H-pyran-4-yl]amino}-N-(3-carbamoyl-1-methyl-1H-pyrazol-4-yl)pyrazolo[1,5-a]pyrimidine-3-carboxamide trifluoroacetate | Calc'd 400.2, found 400.4. |
| 3 | 32 | 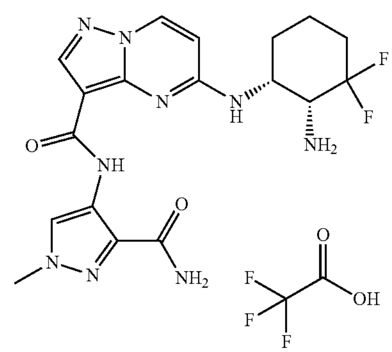 [SMILES: Cn1cc(NC(=O)c2cnn3ccc(N[C@@H]4CCCC(F)(F)[C@@H]4N)nc23)c(C(N)=O)n1 ; O=C(O)C(F)(F)F] | 5-{[(1R,2R)-2-amino-3,3-difluorocyclohexyl]amino}-N-(3-carbamoyl-1-methyl-1H-pyrazol-4-yl)pyrazolo[1,5-a]pyrimidine-3-carboxamide trifluoroacetate | Calc'd 434.2, found 434.2. |
| 4 | 5 | 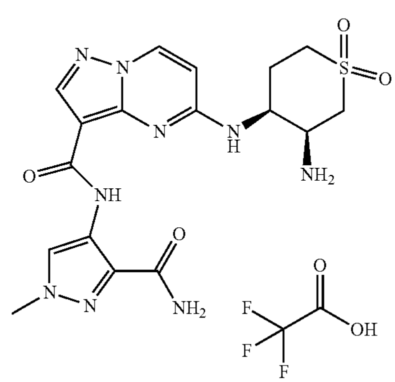 [SMILES: Cn1cc(NC(=O)c2cnn3ccc(N[C@H]4CCS(=O)(=O)C[C@H]4N)nc23)c(C(N)=O)n1 ; O=C(O)C(F)(F)F] | 5-{[cis-3-amino-1,1-dioxidotetrahydro-2H-thiopyran-4-yl]amino}-N-(3-carbamoyl-1-methyl-1H-pyrazol-4-yl)pyrazolo[1,5-a]pyrimidine-3-carboxamide trifluoroacetate | Calc'd 448.2, found 448.2 |

-continued

| Example # | IRAK4 IC$_{50}$ (nM) | Structure | IUPAC Name | Exact Mass [M + H]$^+$ |
|---|---|---|---|---|
| 5 | 15 | 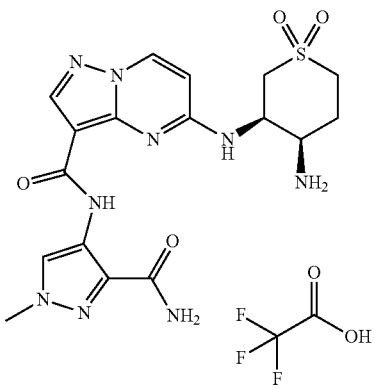 [SMILES: Cn1cc(NC(=O)c2cnn3ccc(N[C@H]4CS(=O)(=O)CC[C@H]4N)nc23)c(C(N)=O)n1 ; O=C(O)C(F)(F)F] | 5-{[cis-4-amino-1,1-dioxidotetrahydro-2H-thiopyran-3-yl]amino}-N-(3-carbamoyl-1-methyl-1H-pyrazol-4-yl)pyrazolo[1,5-a]pyrimidine-3-carboxamide trifluoroacetate | Calc'd 448.2, found 448.2 |
| 6 | 0.8 | 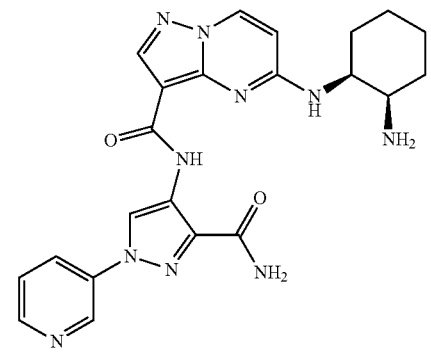 [SMILES: NC(=O)c1nn(-c2cccnc2)cc1NC(=O)c1cnn2ccc(N[C@H]3CCCC[C@H]3N)nc12] | 5-{[cis-2-aminocyclohexyl]amino}-N-(3-carbamoyl-1-pyridin-3-yl-1H-pyrazol-4-yl)pyrazolo[1,5-a]pyrimidine-3-carboxamide | Calc'd 461, found 461 |
| 7 | 8 | 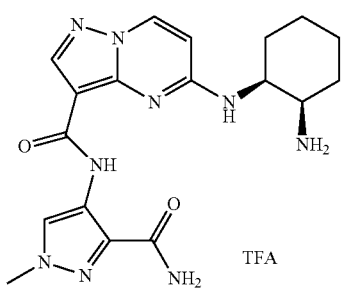 [SMILES: Cn1cc(NC(=O)c2cnn3ccc(N[C@H]4CCCC[C@H]4N)nc23)c(C(N)=O)n1] | 5-{[(1S,2R)-2-aminocyclohexyl]amino}-N-(3-carbamoyl-1-methyl-1H-pyrazol-4-yl)pyrazolo[1,5-a]pyrimidine-3-carboxamide trifluoroacetate | Calc'd 398.2, found 398.0 |
| 8 | 20 | 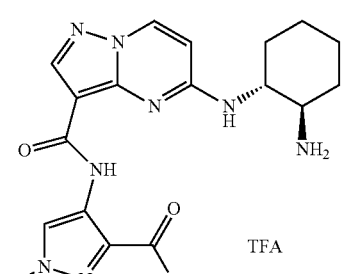 | 5-{[trans-2-aminocyclohexyl]amino}-N-(3-carbamoyl-1-methyl-1H-pyrazol-4-yl)pyrazolo[1,5-a]pyrimidine-3-carboxamide trifluoroacetate | Calc'd 398.2, found 398.0 |

| Example # | IRAK4 IC$_{50}$ (nM) | Structure | IUPAC Name | Exact Mass [M + H]$^+$ |
|---|---|---|---|---|
| 9 | 0.4 | 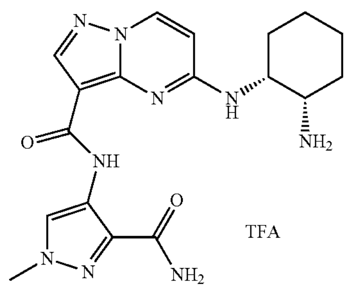 [SMILES: Cn1cc(NC(=O)c2cnn3ccc(N[C@@H]4CCCC[C@@H]4N)nc23)c(C(N)=O)n1] | 5-{[(1R,2S)-2-aminocyclohexyl]amino}-N-(3-carbamoyl-1-methyl-1H-pyrazol-4-yl)pyrazolo[1,5-a]pyrimidine-3-carboxamide trifluoroacetate | Calc'd 398.2, found 398.0 |
| 10 | 25 | 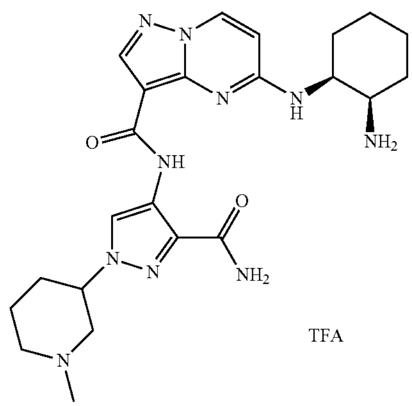 [SMILES: CN1CCCC(n2cc(NC(=O)c3cnn4ccc(N[C@H]5CCCC[C@H]5N)nc34)c(C(N)=O)n2)C1] | 5-{[cis-2-aminocyclohexyl]amino}-N-[3-carbamoyl-1-(1-methylpiperidin-3-yl)-1H-pyrazol-4-yl]pyrazolo[1,5-a]pyrimidine-3-carboxamide trifluoroacetate | Calc'd 481, found 481 |
| 11 | 0.7 | 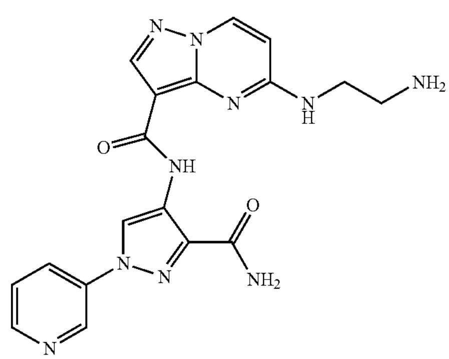 [SMILES: NCCNc1ccn2ncc(C(=O)Nc3cn(-c4cccnc4)nc3C(N)=O)c2n1] | 5-[(2-aminoethyl)amino]-N-(3-carbamoyl-1-pyridin-3-yl-1H-pyrazol-4-yl)pyrazolo[1,5-a]pyrimidine-3-carboxamide | Calc'd 407, found 407 |
| 12 | 95 | 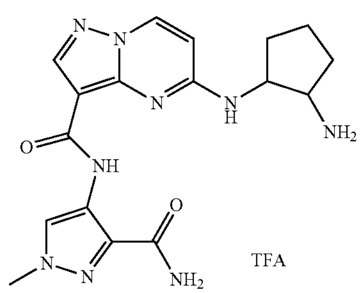 [SMILES: Cn1cc(NC(=O)c2cnn3ccc(NC4CCCC4N)nc23)c(C(N)=O)n1] | 5-[(2-aminocyclopentyl)amino]-N-(3-carbamoyl-1-methyl-1H-pyrazol-4-yl)pyrazolo[1,5-a]pyrimidine-3-carboxamide trifluoroacetate | Calc'd 384, found 384 |

-continued

| Example # | IRAK4 IC$_{50}$ (nM) | Structure | IUPAC Name | Exact Mass [M + H]$^+$ |
|---|---|---|---|---|
| 13 | 2 | 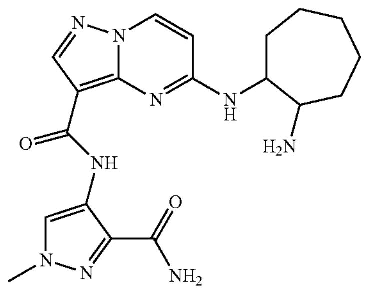 [SMILES: Cn1cc(NC(=O)c2cnn3ccc(NC4CCCCCC4N)nc23)c(C(N)=O)n1] | 5-[(2-aminocycloheptyl)amino]-N-(3-carbamoyl-1-methyl-1H-pyrazol-4-yl)pyrazolo[1,5-a]pyrimidine-3-carboxamide | Calc'd 412, found 412 |
| 14 | 120 | 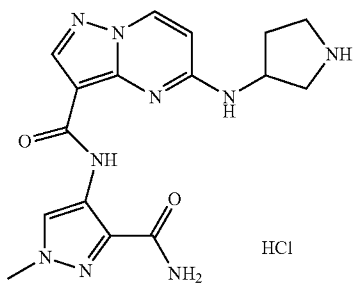 [SMILES: Cn1cc(NC(=O)c2cnn3ccc(NC4CCNC4)nc23)c(C(N)=O)n1 ; Cl] | N-(3-carbamoyl-1-methyl-1H-pyrazol-4-yl)-5-(pyrrolidin-3-ylamino)pyrazolo[1,5-a]pyrimidine-3-carboxamide hydrochloride | Calc'd 370, found 370 |
| 15 | 33 | 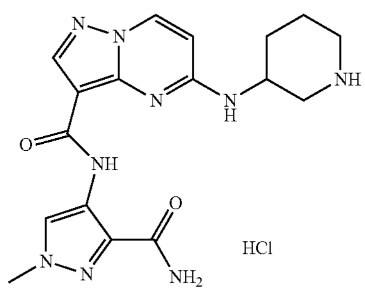 [SMILES: Cn1cc(NC(=O)c2cnn3ccc(NC4CCCNC4)nc23)c(C(N)=O)n1 ; Cl] | N-(3-carbamoyl-1-methyl-1H-pyrazol-4-yl)-5-(piperidin-3-ylamino)pyrazolo[1,5-a]pyrimidine-3-carboxamide hydrochloride | Calc'd 384, found 384 |
| 16 | 18 | 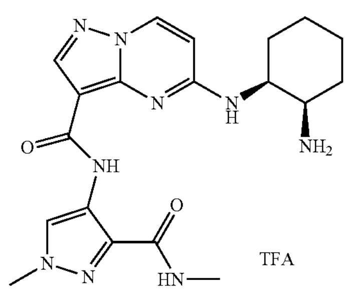 [SMILES: CNC(=O)c1nn(C)cc1NC(=O)c1cnn2ccc(N[C@H]3CCCC[C@H]3N)nc12] | 5-{[cis-2-aminocyclohexyl]amino}-N-[1-methyl-3-(methylcarbamoyl)-1H-pyrazol-4-yl]pyrazolo[1,5-a]pyrimidine-3-carboxamide trifluoroacetate | Calc'd 412, found 412 |
| 17 | 150 | 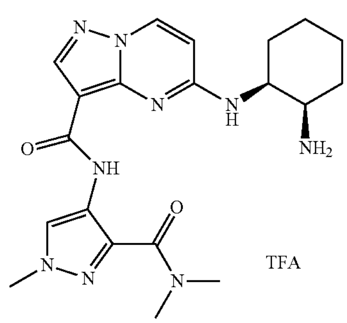 [SMILES: CN(C)C(=O)c1nn(C)cc1NC(=O)c1cnn2ccc(N[C@H]3CCCC[C@H]3N)nc12] | 5-{[cis-2-aminocyclohexyl]amino}-N-[3-(dimethylcarbamoyl)-1-methyl-1H-pyrazol-4-yl]pyrazolo[1,5-a]pyrimidine-3-carboxamide trifluoroacetate | Calc'd 426, found 426 |

Example 18

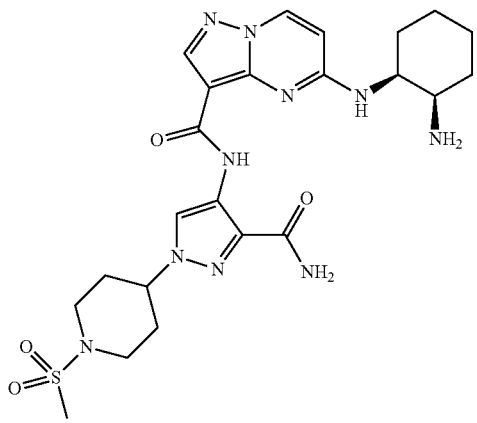 [SMILES: CS(=O)(=O)N1CCC(n2cc(NC(=O)c3cnn4ccc(N[C@H]5CCCC[C@H]5N)nc34)c(C(N)=O)n2)CC1]

5-{[cis-2-Aminocyclohexyl]amino}-N-{3-carbamoyl-1-[1-(methylsulfonyl)piperidin-4-yl]-1H-pyrazol-4-yl}pyrazolo[1,5-a]pyrimidine-3-carboxamide (IRAK4 $IC_{50}$=2 nM)

Step 1. Into a 25 mL round-bottom flask was placed a solution of tert-butyl 4-(4-amino-3-carbamoyl-1H-pyrazol-1-yl)piperidine-1-carboxylate (180 mg, 0.58 mmol), 5-chloropyrazolo[1,5-a]pyrimidine-3-carbonyl chloride (150 mg, 0.69 mmol), 4-dimethylaminopyridine (14.2 mg, 0.12 mmol), and N,N-diisopropylethylamine (225 mg, 1.74 mmol) in dichloromethane (5 mL). The resulting solution was stirred for 1 h at room temperature. The solids were collected by filtration and dried under reduced pressure. This resulted in tert-butyl 4-(3-carbamoyl-4-[5-chloropyrazolo[1,5-a] pyrimidine-3-amido]-1H-pyrazol-1-yl) piperidine-1-carboxylate as a solid. MS $[M+H]^+$ 489.

Step 2. Into a 25 mL round-bottom flask was placed a solution of tert-butyl 4-(3-carbamoyl-4-[5-chloropyrazolo[1,5-a] pyrimidine-3-amido]-1H-pyrazol-1-yl) piperidine-1-carboxylate (300 mg, 0.61 mmol) in dichloromethane (4 mL). This was followed by the addition of trifluoroacetic acid (1 mL) at room temperature. The resulting solution was stirred for 1 h at room temperature. The resulting solution was concentrated under reduced pressure. This resulted in (crude) of N-[3-carbamoyl-1-(piperidin-4-yl)-1H-pyrazol-4-yl]-5-chloropyrazolo[1,5-a]pyrimidine-3-carboxamide trifluoroacetate as an oil. MS $[M+H]^+$ 389.

Step 3. Into a 25 mL round-bottom flask was placed a solution of N-[3-carbamoyl-1-(piperidin-4-yl)-1H-pyrazol-4-yl]-5-chloropyrazolo[1,5-a]pyrimidine-3-carboxamide (180 mg, 0.46 mmol) and triethylamine (140.6 mg, 1.39 mmol) in dichloromethane (5 mL). This was followed by the addition of methanesulfonyl chloride (79 mg, 0.69 mmol) dropwise with stirring at 0° C. The resulting solution was stirred for 1 h at room temperature. The resulting solution was diluted with dichloromethane, washed with water, dried over $Na_2SO_4$, filtered and concentrated under reduced pressure. The residue was purified by flash chromatography on a silica gel column, eluting with dichloromethane/methanol (100:1-20:1). This resulted in N-{3-carbamoyl-1-[1-(methylsulfonyl)piperidin-4-yl]-1H-pyrazol-4-yl}-5-chloropyrazolo[1,5-a]pyrimidine-3-carboxamide as a solid. MS $[M+H]^+$ 467.

Step 4. Into a 25 mL round-bottom flask was placed a solution of N-{3-carbamoyl-1-[1-(methylsulfonyl)piperidin-4-yl]-1H-pyrazol-4-yl}-5-chloropyrazolo[1,5-a]pyrimidine-3-carboxamide (50 mg, 0.11 mmol) in acetonitrile (2 mL), then cis-cyclohexane-1,2-diamine (48.9 mg, 0.43 mmol) was added. The resulting solution was stirred for 1 h at 50° C. After removal of the solvent, the residue (50 mg) was purified by Prep-HPLC. This resulted in 5-{[cis-2-aminocyclohexyl]amino}-N-{3-carbamoyl-1-[1-(methylsulfonyl)piperidin-4-yl]-1H-pyrazol-4-yl}pyrazolo[1,5-a] pyrimidine-3-carboxamide trifluoroacetate as a solid. $^1$H NMR (400 MHz, $D_2O$): δ 1.34-1.52 (m, 4H), 1.66-1.74 (m, 4H), 1.84-1.97 (m, 2H), 2.14-2.20 (m, 2H), 2.89-2.95 (m, 5H), 3.51-3.57 (m, 1H), 3.71-3.73 (d, J=11.2 Hz, 2H), 4.26-4.29 (m, 1H), 4.90-5.00 (m, 1H), 6.26-6.27 (d, J=7.2 Hz, 1H), 7.88 (s, 1H), 7.97-7.99 (d, J=7.2 Hz, 1H), 8.09 (s, 1H). MS $[M+H]^+$ 545.

Example 19

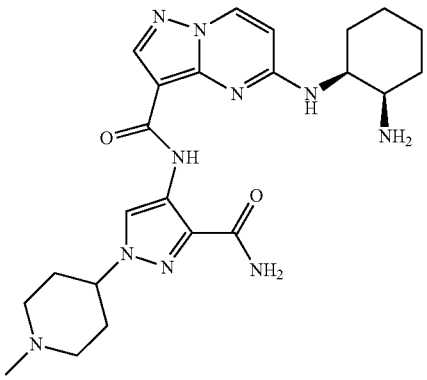 [SMILES: CN1CCC(n2cc(NC(=O)c3cnn4ccc(N[C@H]5CCCC[C@H]5N)nc34)c(C(N)=O)n2)CC1]

5-{[cis-2-Aminocyclohexyl]amino}-N-[3-carbamoyl-1-(1-methylpiperidin-4-yl)-1H-pyrazol-4-yl] pyrazolo[1,5-a]pyrimidine-3-carboxamide (IRAK4 $IC_{50}$=2 nM)

Step 1. Into a 10 mL round-bottom flask was placed a solution of N-[3-carbamoyl-1-(piperidin-4-yl)-1H-pyrazol-4-yl]-5-chloropyrazolo[1,5-a]pyrimidine-3-carboxamide (390 mg, 1.00 mmol) and formaldehyde (90.5 mg, 3.01 mmol) in methanol (5 mL). The resulting solution was stirred for 30 min at room temperature. Sodium cyanoborohydride (189 mg, 3.02 mmol) was added. The resulting solution was allowed to stir for an additional 1 h at room temperature. The resulting mixture was concentrated under reduced pressure. This resulted in crude N-[3-carbamoyl-1-(1-methylpiperidin-4-yl)-1H-pyrazol-4-yl]-5-chloropyrazolo[1,5-a]pyrimidine-3-carboxamide as a solid. MS $[M+H]^+$ 403.

Step 2. Into a 25 mL round-bottom flask was placed a solution of crude N-[3-carbamoyl-1-(1-methylpiperidin-4-yl)-1H-pyrazol-4-yl]-5-chloropyrazolo[1,5-a]pyrimidine-3-carboxamide (300 mg) in acetonitrile (5 mL), and then cis-cyclohexane-1,2-diamine (340 mg, 2.98 mmol) was added. The resulting solution was stirred for 1 h at 50° C. The resulting mixture was concentrated under reduced pressure. The residue was purified by Prep-HPLC. This resulted in 5-{[cis-2-aminocyclohexyl]amino}-N-[3-carbamoyl-1-(1-methylpiperidin-4-yl)-1H-pyrazol-4-yl]pyrazolo[1,5-a]

pyrimidine-3-carboxamide trifluoroacetate as a solid. ¹H NMR (400 MHz, D₂O): δ 1.20-1.60 (m, 4H), 1.60-1.92 (m, 4H), 2.22-2.55 (m, 4H), 2.84-2.87 (m, 3H), 3.08-3.35 (m, 2H), 3.44-3.55 (m, 1H), 3.63-3.66 (m, 2H), 4.20 (br, 1H), 4.97 (s, 1H), 6.25-6.26 (d, J=7.2 Hz, 1H), 7.95-7.99 (m, 2H), 8.19-8.21 (m, 1H). MS [M+H]⁺ 481.

The following example was prepared in an analogous manner of that described in Example 18.

| Example # | IRAK4 IC$_{50}$ (nM) | Structure | IUPAC Name | Exact Mass [M + H]⁺ |
|---|---|---|---|---|
| 20 | 4 | 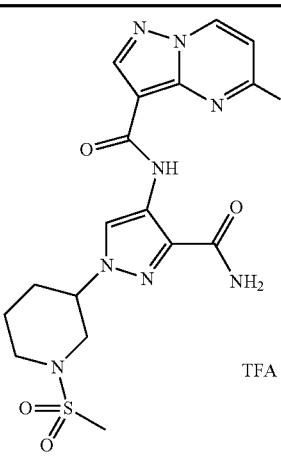 | 5-{[cis-2-aminocyclohexyl]amino}-N-{3-carbamoyl-1-[1-(methylsulfonyl)piperidin-3-yl]-1H-pyrazol-4-yl}pyrazolo[1,5-a]pyrimidine-3-carboxamide trifluoroacetate | Calc'd 545, found 545 |

Example 21

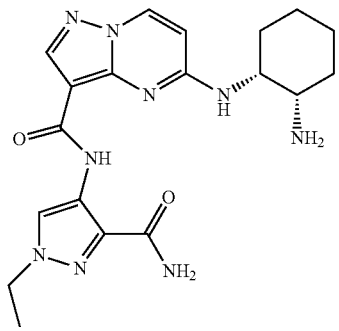 [SMILES: CCn1cc(NC(=O)c2cnn3ccc(N[C@@H]4CCCC[C@@H]4N)nc23)c(C(N)=O)n1]

5-{[(1R,2S)-2-Aminocyclohexyl]amino}-N-(3-carbamoyl-1-ethyl-1H-pyrazol-4-yl)pyrazolo[1,5-a]pyrimidine-3-carboxamide (IRAK4 IC$_{50}$=0.6 nM)

Step 1. Into a 25 mL sealed tube were added ethyl 5-chloropyrazolo[1,5-a]pyrimidine-3-carboxylate (500 mg, 2.2 mmol), tert-butyl ((1S,2R)-2-aminocyclohexyl)carbamate (475 mg, 2.2 mmol) and ethanol (5 mL) and the resulting solution was stirred at 90° C. for 8 h. The reaction mixture was cooled to room temperature and concentrated under reduced pressure. The crude product was purified by flash chromatography eluting with ethyl acetate in petroleum ether (20-30%) to yield ethyl 5-(((1R,2S)-2-((tert-butoxycarbonyl)amino)cyclohexyl)amino)pyrazolo[1,5-a]pyrimidine-3-carboxylate as a solid. ¹H NMR (DMSO-d₆, 400 MHz): δ 8.48 (d, J=7.5 Hz, 1H), 8.12 (s, 1H), 7.48 (d, J=7.3 Hz, 1H), 6.61 (d, J=8.3 Hz, 1H), 6.45 (d, J=7.5 Hz, 1H), 4.31-4.22 (m, 1H), 4.17 (q, J=6.7 Hz, 2H), 4.03-4.01 (m, 1H), 1.85-1.48 (m, 8H), 1.36 (s, 9H), 1.31 (t, J=6.7 Hz, 3H). MS calc'd [M+H]⁺ 404.2, found 404.4.

Step 2. Into a 25 mL round bottom flask containing a solution of ethyl 5-(((1R,2S)-2-((tert-butoxycarbonyl)amino)cyclohexyl)amino)pyrazolo[1,5-a]pyrimidine-3-carboxylate (500 mg, 1.24 mmol) in tetrahydrofuran (2 mL) and water (5 mL) mixture was added lithium hydroxide (156 mg, 3.72 mmol) and stirred for 12 h. Reaction mixture was diluted with water and extracted with ethyl acetate. The combined organic fractions were concentrated and the crude product was purified by column chromatography eluting with methanol in dichloromethane (2%) to afford 5-(((1R,2S)-2-((tert-butoxycarbonyl)amino)cyclohexyl)amino)pyrazolo[1,5-a]pyrimidine-3-carboxylic acid as a liquid. ¹H NMR (DMSO-d₆, 300 MHz): δ 11.45 (s, 1H), 8.49 (d, J=7.1 Hz, 1H), 8.09 (s, 1H), 7.48 (brs, 1H), 6.6 (brs, 1H), 6.47 (d, J=7.2 Hz, 1H), 4.29-4.26 (m, 1H), 3.83-3.80 (m, 1H), 1.79-1.54 (m, 5H), 1.35-1.21 (12H). MS calc'd [M+H]⁺ 376.2, found 376.4.

Step 3. Into a 25 mL round bottom flask containing a solution of 5-(((1R,2S)-2-((tert-butoxycarbonyl)amino)cyclohexyl)amino)pyrazolo[1,5-a]pyrimidine-3-carboxylic acid (80 mg, 0.21 mmol,) in acetonitrile (5 mL) were added N,N-diisopropylethylamine (0.073 mL, 0.43 mmol) and 4-amino-1-ethyl-1H-pyrazole-3-carboxamide (40 mg, 0.26 mmol) followed by the addition of HATU (122 mg, 0.32 mmol) and stirred at 80° C. for 12 h. The reaction mixture was cooled to room temperature, diluted with water and extracted with ethyl acetate. The combined organic layers were washed with water and brine, dried over anhydrous sodium sulfate, filtered and concentrated. The residue was purified by flash chromatography eluting with methanol in chloroform (2-5%) to afford tert-butyl ((1R,2S)-2-((3-((3-carbamoyl-1-ethyl-1H-pyrazol-4-yl)carbamoyl)pyrazolo[1,5-a]pyrimidin-5-yl)amino)cyclohexyl)carbamate as a solid. ¹H NMR (DMSO-d₆, 300 MHz): δ 10.6 (s, 1H), 8.48 (d, J=7.2 Hz, 1H), 8.32 (s, 1H), 8.14 (s, 1H), 7.53 (brs, 1H), 7.44 (s, 1H), 7.13 (s, 1H), 6.47-6.44 (m, 2H), 4.89-4.87 (m, 1H), 4.18 (q, J=7.0 Hz, 2H), 3.99-3.97 (m, 1H), 1.97-1.89 (m, 8H), 1.27 (s, 9H), 1.15 (t, J=7.1 Hz, 3H). MS calc'd [M+H]⁺ 512.3, found 512.0.

Step 4. Into a 10 mL round bottom flask containing a solution of tert-butyl ((1R,2S)-2-((3-((3-carbamoyl-1-ethyl-1H-pyrazol-4-yl)carbamoyl)pyrazolo[1,5-a]pyrimidin-5-yl)amino)cyclohexyl)carbamate (90 mg, 0.17 mmol) in anhydrous 1,4-dioxane (1 mL) was added hydrochloric acid (4.4 M in dioxane, 1 mL) and stirred for 2 h at room temperature. The solvent was removed under reduced pressure and the residue was purified by preparative HPLC to afford 5-(((1R,2S)-2-aminocyclohexyl)amino)-N-(3-carbamoyl-1-ethyl-1H-pyrazol-4-yl)pyrazolo[1,5-a]pyrimidine-3-carboxamide trifluoroacetate. $^1$H NMR (DMSO-$d_6$, 400 MHz): δ 8.63 (d, J=7.6 Hz, 1H), 8.40 (s, 1H), 8.22 (s, 1H), 7.97 (s, 1H), 7.83-7.81 (m, 1H), 7.70 (s, 1H), 7.62 (brs, 3H), 6.67 (d, J=7.6 Hz, 1H), 5.21 (brs, 1H), 4.21 (q, J=7.2 Hz, 2H), 3.71-3.60 (m, 1H), 1.78-1.51 (m, 8H), 1.41 (t, J=7.2 Hz, 3H). MS calc'd [M+H]$^+$ 412.2, found 412.4.

The following examples were prepared in an analogous manner of that described in Example 21.

| Example # | IRAK4 IC$_{50}$ (nM) | Structure | IUPAC Name | Exact Mass [M + H]$^+$ |
|---|---|---|---|---|
| 22 | 1 | 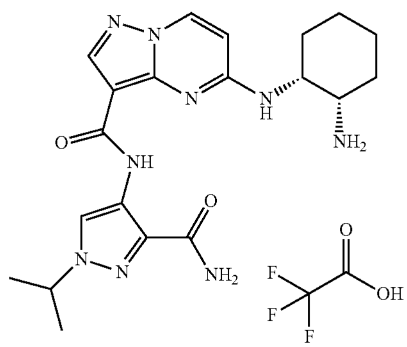 [SMILES: CC(C)n1cc(NC(=O)c2cnn3ccc(N[C@@H]4CCCC[C@@H]4N)nc23)c(C(N)=O)n1 ; O=C(O)C(F)(F)F] | 5-{[(1R,2S)-2-aminocyclohexyl]amino}-N-[3-carbamoyl-1-(1-methylethyl)-1H-pyrazol-4-yl]pyrazolo[1,5-a]pyrimidine-3-carboxamide trifluoroacetate | Calc'd 426.2, found 426.4 |
| 23 | 1 | 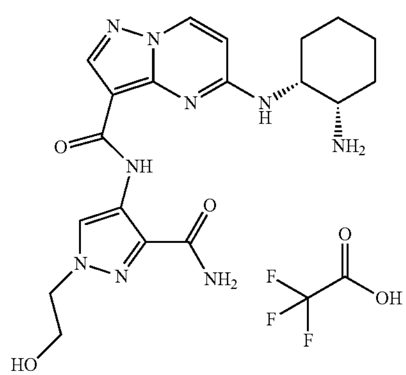 [SMILES: NC(=O)c1nn(CCO)cc1NC(=O)c1cnn2ccc(N[C@@H]3CCCC[C@@H]3N)nc12 ; O=C(O)C(F)(F)F] | 5-{[(1R,2S)-2-aminocyclohexyl]amino}-N-[3-carbamoyl-1-(2-hydroxyethyl)-1H-pyrazol-4-yl]pyrazolo[1,5-a]pyrimidine-3-carboxamide trifluoroacetate | Calc'd 428.2, found 428.4 |
| 24 | 3 | 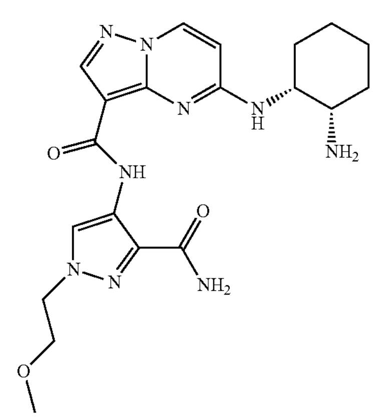 [SMILES: COCCn1cc(NC(=O)c2cnn3ccc(N[C@@H]4CCCC[C@@H]4N)nc23)c(C(N)=O)n1] | 5-{[(1R,2S)-2-aminocyclohexyl]amino}-N-[3-carbamoyl-1-(2-methoxyethyl)-1H-pyrazol-4-yl]pyrazolo[1,5-a]pyrimidine-3-carboxamide | Calc'd 442.2, found 442.4 |

-continued

| Example # | IRAK4 IC$_{50}$ (nM) | Structure | IUPAC Name | Exact Mass [M + H]$^+$ |
|---|---|---|---|---|
| 25 | 2 | 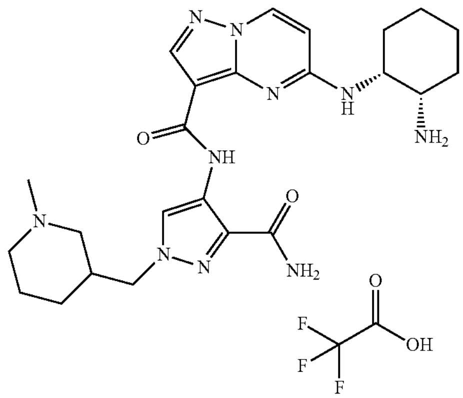 | 5-{[(1R,2S)-2-aminocyclohexyl]amino}-N-{3-carbamoyl-1-[(1-methylpiperidin-3-yl)methyl]-1H-pyrazol-4-yl}pyrazolo[1,5-a]pyrimidine-3-carboxamide trifluoroacetate | Calc'd 495.3, found 495.4. |
| 26 | 180 | 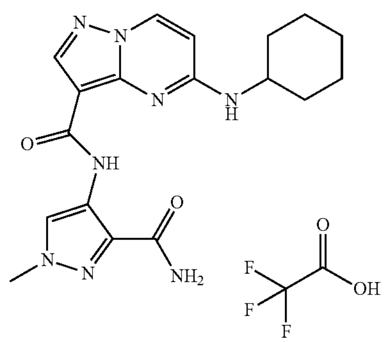 [SMILES: Cn1cc(NC(=O)c2cnn3ccc(NC4CCCCC4)nc23)c(C(N)=O)n1 ; O=C(O)C(F)(F)F] | N-(3-carbamoyl-1-methyl-1H-pyrazol-4-yl)-5-(cyclohexylamino)pyrazolo[1,5-a]pyrimidine-3-carboxamide trifluoroacetate | Calc'd 383.2, found 383.4 |
| 27 | 210 | 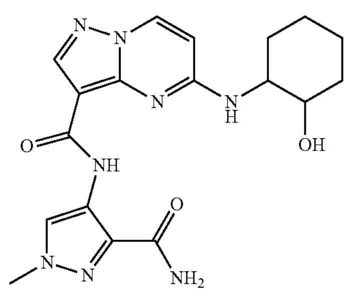 [SMILES: Cn1cc(NC(=O)c2cnn3ccc(NC4CCCCC4O)nc23)c(C(N)=O)n1] | N-(3-carbamoyl-1-methyl-1H-pyrazol-4-yl)-5-[(2-hydroxycyclohexyl)amino]pyrazolo[1,5-a]pyrimidine-3-carboxamide | Calc'd 399, found 399 |
| 28 | 2 | 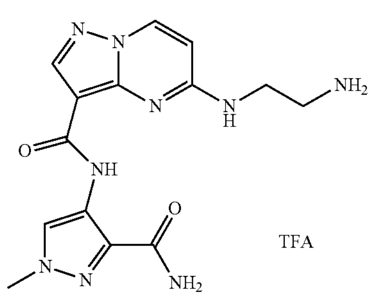 [SMILES: Cn1cc(NC(=O)c2cnn3ccc(NCCN)nc23)c(C(N)=O)n1] | 5-[(2-aminoethyl)amino]-N-(3-carbamoyl-1-methyl-1H-pyrazol-4-yl)pyrazolo[1,5-a]pyrimidine-3-carboxamide trifluoroacetate | Calc'd 344, found 344 |

| Example # | IRAK4 IC$_{50}$ (nM) | Structure | IUPAC Name | Exact Mass [M + H]$^+$ |
|---|---|---|---|---|
| 29 | 270 | 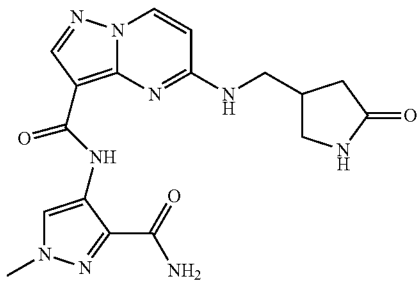 [SMILES: Cn1cc(NC(=O)c2cnn3ccc(NCC4CNC(=O)C4)nc23)c(C(N)=O)n1] | N-(3-carbamoyl-1-methyl-1H-pyrazol-4-yl)-5-{[(5-oxopyrrolidin-3-yl)methyl]amino}pyrazolo[1,5-a]pyrimidine-3-carboxamide | Calc'd 398, found 398 |
| 30 | 240 | 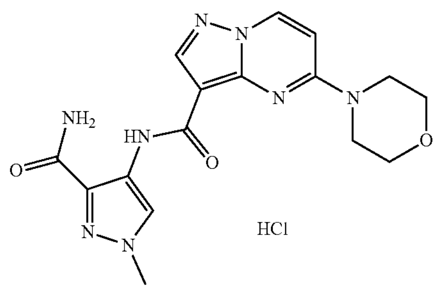 [SMILES: Cn1cc(NC(=O)c2cnn3ccc(N4CCOCC4)nc23)c(C(N)=O)n1 ; Cl] | N-(3-carbamoyl-1-methyl-1H-pyrazol-4-yl)-5-morpholin-4-ylpyrazolo[1,5-a]pyrimidine-3-carboxamide hydrochloride | Calc'd 371, found 371 |
| 31 | 37 | 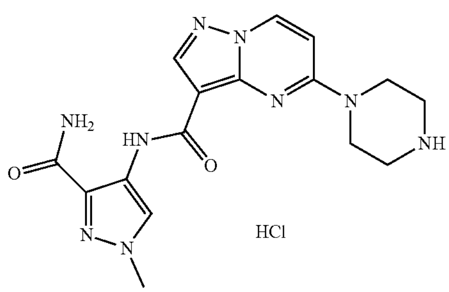 [SMILES: Cn1cc(NC(=O)c2cnn3ccc(N4CCNCC4)nc23)c(C(N)=O)n1 ; Cl] | N-(3-carbamoyl-1-methyl-1H-pyrazol-4-yl)-5-piperazin-1-ylpyrazolo[1,5-a]pyrimidine-3-carboxamide hydrochloride | Calc'd 370, found 370 |

Example 32

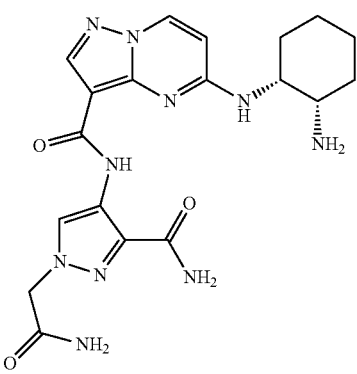 [SMILES: NC(=O)Cn1cc(NC(=O)c2cnn3ccc(N[C@@H]4CCCC[C@@H]4N)nc23)c(C(N)=O)n1]

5-{[(1R,2S)-2-Aminocyclohexyl]amino}-N-[1-(2-amino-2-oxoethyl)-3-carbamoyl-1H-pyrazol-4-yl]pyrazolo[1,5-a]pyrimidine-3-carboxamide (IRAK4 IC$_{50}$=3 nM)

Step 1. Into a 25 mL round bottom flask containing a solution of 5-(((1R,2S)-2-((tert-butoxycarbonyl)amino)cyclohexyl)amino)pyrazolo[1,5-a]pyrimidine-3-carboxylic acid (125 mg, 0.3 mmol) in acetonitrile (5 mL) were added N,N-diisopropylethylamine (0.1 mL, 0.6 mmol) and ethyl 2-(4-amino-3-carbamoyl-1H-pyrazol-1-yl)acetate (80 mg, 0.4 mmol) followed by the addition of HATU (190 mg, 0.5 mmol) and stirred at 60° C. for 12 h. The reaction mixture was cooled to room temperature, diluted with water and extracted with ethyl acetate. The combined organic layers were washed with water and brine, dried over anhydrous sodium sulfate, filtered and concentrated. The residue was purified by flash chromatography eluting with methanol in chloroform (2-5%) to afford methyl [4-({[5-({(1R,2S)-2-[(tert-butoxycarbonyl)amino]cyclohexyl}amino)pyrazolo[1,5-a]pyrimidin-3-yl]carbonyl}amino)-3-carbamoyl-1H-pyrazol-1-yl]acetate as a solid. $^1$H NMR (DMSO-d$_6$, 400 MHz): δ 10.65 (s, 1H), 8.51 (d, J=7.1 Hz, 1H), 8.45 (s, 1H), 8.17 (s, 1H), 7.58-7.54 (m, 2H), 7.22 (s, 1H), 6.52-6.44 (m, 2H), 5.18 (s, 2H), 4.96-4.91 (m, 1H), 4.08-4.00 (m, 1H), 3.71 (s, 3H), 1.59-1.51 (m, 8H), 1.41 (s, 9H). MS calc'd [M+H]$^+$ 556.3, found 556.2.

Step 2. A mixture of methyl [4-({[5-({(1R,2S)-2-[(tert-butoxycarbonyl)amino]cyclohexyl}amino)pyrazolo[1,5-a]pyrimidin-3-yl]carbonyl}amino)-3-carbamoyl-1H-pyrazol-1-yl]acetate (110 mg, 0.2 mmol) and aqueous ammonia (10 mL) in 25 mL round bottom flask was heated at 110° C. for 4 h. The reaction mixture was concentrated under reduced pressure to afford tert-butyl {(1S,2R)-2-[(3-{[1-(2-amino-2-oxoethyl)-3-carbamoyl-1H-pyrazol-4-yl]carbamoyl}pyrazolo[1,5-a]pyrimidin-5-yl)amino]cyclohexyl}carbamate which was taken to next step without further purification. $^1$H NMR (DMSO-d$_6$, 400 MHz): δ 10.60 (s, 1H), 8.49 (d, J=6.4 Hz, 1H), 8.23 (s, 1H), 8.15 (s, 1H), 7.52 (d, J=6.4 Hz, 1H), 7.42 (s, 1H), 7.13-7.03 (m, 2H), 6.46-6.44 (m, 2H), 4.91-4.89 (m, 1H), 4.52 (s, 2H), 4.01-3.98 (m, 1H), 1.68-1.51 (m, 8H), 1.30 (s, 9H). MS calc'd [M+H]$^+$ 541.3, found 541.0.

Step 3. Into a 10 mL round bottom flask containing a solution tert-butyl ((1S,2R)-2-((3-((1-(2-amino-2-oxoethyl)-3-carbamoyl-1H-pyrazol-4-yl)carbamoyl)pyrazolo[1,5-a]pyrimidin-5-yl)amino)cyclohexyl)carbamate (90 mg, 0.17 mmol) in anhydrous 1,4-dioxane (1 mL) was added hydrochloric acid (4.4 M in dioxane, 1 mL) and stirred for 2 h at room temperature. The solvent was removed under reduced pressure and the residue was purified by preparative HPLC to afford 5-{[(1R,2S)-2-aminocyclohexyl]amino}-N-[1-(2-amino-2-oxoethyl)-3-carbamoyl-1H-pyrazol-4-yl]pyrazolo[1,5-a]pyrimidine-3-carboxamide trifluoroacetate. $^1$H NMR (DMSO-d$_6$, 400 MHz): δ 8.62 (d, J=7.6 Hz, 1H), 8.38 (s, 1H), 8.22 (s, 1H), 7.99 (s, 1H), 7.83-7.81 (m, 1H), 7.7 (s, 1H), 7.62-7.58 (m, 4H), 7.30 (s, 1H), 6.65 (d, J=7.6 Hz, 1H), 5.21-5.20 (m, 1H), 4.86 (s, 2H), 1.78-1.53 (m, 8H). MS calc'd [M+H]$^+$ 441.2, found 441.4.

Example 33

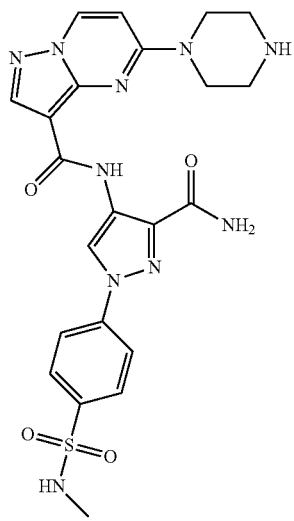 [SMILES: CNS(=O)(=O)c1ccc(-n2cc(NC(=O)c3cnn4ccc(N5CCNCC5)nc34)c(C(N)=O)n2)cc1]

N-{3-Carbamoyl-1-[4-(methylsulfamoyl)phenyl]-1H-pyrazol-4-yl}-5-piperazin-1-ylpyrazolo[1,5-a]pyrimidine-3-carboxamide (IRAK4 IC$_{50}$=4 nM)

Step 1. Into a 50 mL round-bottom flask was placed a solution of ethyl 5-chloropyrazolo[1,5-a]pyrimidine-3-carboxylate (840 mg, 3.54 mmol), tert-butyl piperazine-1-carboxylate (1.04 g, 5.53 mmol), and N,N-diisopropylethylamine (1.44 g, 11.03 mmol) in acetonitrile (10 mL). The resulting solution was stirred for 2 h at 60° C. in an oil bath. After removal of the solvent, the residue was purified by flash chromatography on silica gel, eluting with a mixture of 50% ethyl acetate in petroleum ether (1:1). This resulted in tert-butyl 4-[3-(ethoxycarbonyl)pyrazolo[1,5-a]pyrimidin-5-yl]piperazine-1-carboxylate as a solid. MS [M+H]$^+$ 376.

Step 2. Into a 100 mL round-bottom flask was placed a solution of tert-butyl 4-[3-(ethoxycarbonyl)pyrazolo[1,5-a]pyrimidin-5-yl]piperazine-1-carboxylate (1.21 g, 3.06 mmol) and LiOH.H$_2$O (810 mg, 19.11 mmol) in methanol (30 mL). The resulting solution was stirred for 4 days at room temperature. The mixture was acidified with AcOH. The resulting solution was concentrated under reduced pressure. The resulting solution was diluted with 30 mL of H$_2$O. The solids were collected by filtration. This resulted in 5-[4-[(tert-butoxy)carbonyl]piperazin-1-yl]pyrazolo[1,5-a]pyrimidine-3-carboxylic acid as a solid. MS [M+H]$^+$ 348.

Step 3. Into a 50 mL round-bottom flask was placed a solution of ethyl 4-amino-1H-pyrazole-3-carboxylate (330 mg, 2.13 mmol), 5-4-[(tert-butoxy)carbonyl]piperazin-1-ylpyrazolo[1,5-a]pyrimidine-3-carboxylic acid (500 mg, 1.44 mmol) and HATU (900 mg, 2.37 mmol) in N,N-dimethylformamide (20 mL). This was followed by the addition of N,N-diisopropylethylamine (1.25 g, 9.69 mmol) dropwise with stirring. The resulting solution was stirred for 1 h at room temperature and for 2 h at 50° C. in an oil bath. The resulting solution was diluted with 100 mL of ethyl acetate, washed with 3×100 mL of water, dried over Na$_2$SO$_4$, filtered and concentrated under reduced pressure. The residue was purified by flash chromatography on silica gel, eluting with ethyl acetate. This resulted in tert-butyl 4-(3-[[3-(ethoxycarbonyl)-1H-pyrazol-4-yl]carbamoyl]pyrazolo[1,5-a]pyrimidin-5-yl)piperazine-1-carboxylate as a solid. 1H NMR (300 MHz, DMSO-d$_6$): δ 1.23-1.43 (m, 12H), 3.50 (m, 4H), 4.30 (m, 4H), 4.40 (m, 2H), 6.89 (m, 1H), 7.71 (m, 2H), 8.43 (m, 2H), 8.80 (m, 1H). MS [M+H]$^+$ 485.

Step 4. Into a 10 mL sealed tube was placed a solution of tert-butyl 4-(3-[[3-(ethoxycarbonyl)-1H-pyrazol-4-yl]carbamoyl]pyrazolo[1,5-a]pyrimidin-5-yl)piperazine-1-carboxylate (20 mg, 0.04 mmol), [4-(methylsulfamoyl)phenyl]boronic acid (9 mg, 0.04 mmol) and (acetyloxy)cuprio acetate (5 mg, 0.03 mmol) in N,N-dimethylformamide (1 mL). This was followed by the addition of pyridine (4 mg, 0.05 mmol) dropwise with stirring at room temperature. The resulting solution was stirred for 3 h at 80° C. in an oil bath. After concentrated under reduced pressure, the resulting solution was diluted with 50 mL of ethyl acetate. The solids were filtered out. After removal of the solvent, the residue was purified by flash chromatography on silica gel, eluting with a mixture of 1% EtOH in CH$_2$Cl$_2$. This resulted in tert-butyl 4-(3-[[3-(ethoxycarbonyl)-1-[4-(methylsulfamoyl)phenyl]-1H-pyrazol-4-yl]carbamoyl]pyrazolo[1,5-a]pyrimidin-5-yl)piperazine-1-carboxylate as a solid. MS [M+H]$^+$ 654.

Step 5. Into a 10 mL sealed tube was placed tert-butyl 4-(3-[[3-(ethoxycarbonyl)-1-[4-(methylsulfamoyl)phenyl]-1H-pyrazol-4-yl]carbamoyl]pyrazolo[1,5-a]pyrimidin-5-yl)piperazine-1-carboxylate (100 mg, 0.008 mmol) in NH$_3$/MeOH (5 mL, 10M). The resulting solution was stirred for 12 h at 70° C. in an oil bath. The resulting solution was concentrated under reduced pressure. This resulted in tert-butyl 4-[3-([3-carbamoyl-1-[4-(methylsulfamoyl)phenyl]-1H-pyrazol-4-yl]carbamoyl)pyrazolo[1,5-a]pyrimidin-5-yl]piperazine-1-carboxylate as a solid. MS [M+H]$^+$ 625.

Step 6. Into a 25 mL round-bottom flask was placed a solution of tert-butyl 4-[3-([3-carbamoyl-1-[4-(methylsulfamoyl)phenyl]-1H-pyrazol-4-yl]carbamoyl)pyrarazolo[1,5-a]pyrimidin-5-yl]piperazine-1-carboxylate (90 mg, 0.14 mmol) in dichloromethane (5 mL). This was followed by the addition of trifluoroacetic acid (3 mL) dropwise with stirring at room temperature. The resulting solution was stirred for 30 min at room temperature. After removal the solvent, the residue (5 mL) was purified by Prep-HPLC. This resulted in N-{3-carbamoyl-1-[4-(methylsulfamoyl)phenyl]-1H-pyrazol-4-yl}-5-piperazin-1-ylpyrazolo[1,5-a]pyrimidine-3-carboxamide trifluoroacetate as a solid. $^1$H NMR (D$_2$O, 400 MHz): δ 2.42 (s, 3H), 3.28 (s, 4H), 3.90 (s, 4H), 6.16 (d, J=8.0 Hz, 1H), 7.13-7.16 (m, 2H), 7.29-7.35 (m, 2H), 7.85 (d, J=7.6 Hz, 1H), 7.95 (s, 1H), 8.09 (s, 1H). MS [M+H]$^+$ 525.

The following examples were prepared in an analogous manner of that described in Example 33.

| Example # | IRAK4 IC$_{50}$ (nM) | Structure | IUPAC Name | Exact Mass [M + H]$^+$ |
|---|---|---|---|---|
| 34 | 25 | 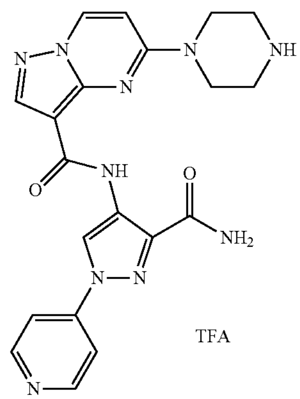 [SMILES: NC(=O)c1nn(-c2ccncc2)cc1NC(=O)c1cnn2ccc(N3CCNCC3)nc12] | N-(3-carbamoyl-1-pyridin-4-yl-1H-pyrazol-4-yl)-5-piperazin-1-ylpyrazolo[1,5-a]pyrimidine-3-carboxamide trifluoroacetate | Calc'd 433, found 433 |
| 35 | 310 | 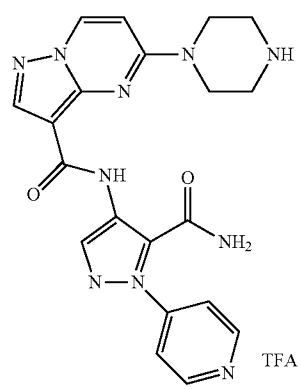 | N-(5-carbamoyl-1-pyridin-4-yl-1H-pyrazol-4-yl)-5-piperazin-1-ylpyrazolo[1,5-a]pyrimidine-3-carboxamide trifluoroacetate | Calc'd 433, found 433 |
| 36 | 33 | 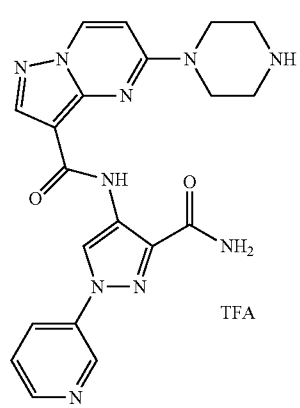 [SMILES: NC(=O)c1nn(-c2cccnc2)cc1NC(=O)c1cnn2ccc(N3CCNCC3)nc12] | N-(3-carbamoyl-1-pyridin-3-yl-1H-pyrazol-4-yl)-5-piperazin-1-ylpyrazolo[1,5-a]pyrimidine-3-carboxamide trifluoroacetate | Calc'd 433, found 433 |

Example 37

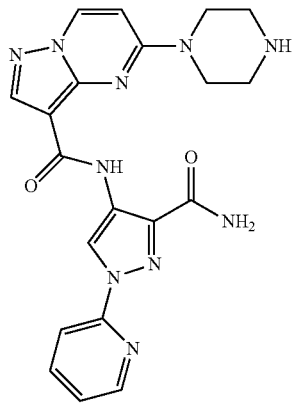 [SMILES: NC(=O)c1nn(-c2ccccn2)cc1NC(=O)c1cnn2ccc(N3CCNCC3)nc12]

N-(3-Carbamoyl-1-pyridin-2-yl-1H-pyrazol-4-yl)-5-piperazin-1-ylpyrazolo[1,5-a]pyrimidine-3-carboxamide (IRAK4 IC$_{50}$=1,000 nM)

Step 1. Into a 10 mL round-bottom flask purged and maintained with an inert atmosphere of nitrogen was placed a solution of tert-butyl 4-(3-[[3-(ethoxycarbonyl)-1H-pyrazol-4-yl]carbamoyl]pyrazolo[1,5-a]pyrimidin-5-yl)piperazine-1-carboxylate (50 mg, 0.10 mmol), 2-fluoropyridine (30 mg, 0.31 mmol) and potassium carbonate (42 mg, 0.30 mmol) in N,N-dimethylformamide (1 mL). The resulting solution was stirred for 12 h at 80° C. in an oil bath. After removal of the solvent, the residue was purified by flash chromatography on silica gel, eluting with a mixture of 5% EtOH in CH$_2$Cl$_2$. This resulted in tert-butyl 4-(3-[[3-(ethoxycarbonyl)-1-(pyridin-2-yl)-1H-pyrazol-4-yl]carbamoyl]pyrazolo[1,5-a]pyrimidin-5-yl) piperazine-1-carboxylate as a solid. MS [M+H]$^+$ 562.

Step 2. Into a 10 mL round-bottom flask was placed tert-butyl 4-(3-[[3-(ethoxycarbonyl)-1-(pyridin-2-yl)-1H-pyrazol-4-yl]carbamoyl]pyrazolo[1,5-a]pyrimidin-5-yl)piperazine-1-carboxylate (70.0 mg, 0.12 mmol) in methanol (3 mL). To the solution, ammonia was introduced in. The resulting solution was stirred for 36 h at 70° C. in an oil bath. After removal of the solvent, this resulted in tert-butyl 4-(3-[[3-carbamoyl-1-(pyridin-2-yl)-1H-pyrazol-4-yl]carbamoyl]pyrazolo[1,5-a]pyrimidin-5-yl)piperazine-1-carboxylate as a solid. The product was used in next step directly. MS [M+H]$^+$ 533.

Step 3. Into a 10 mL round-bottom flask was placed a solution of tert-butyl 4-(3-[[3-carbamoyl-1-(pyridin-2-yl)-1H-pyrazol-4-yl]carbamoyl]pyrazolo[1,5-a]pyrimidin-5-yl) piperazine-1-carboxylate (33.0 mg, 0.06 mmol) and trifluoroacetic acid (0.3 mL) in dichloromethane (1 mL). The resulting solution was stirred for 1 h at 25° C. After removal of the solvent, the residue was purified by Prep-HPLC. This resulted in N-(3-carbamoyl-1-(pyridin-2-yl)-1H-pyrazol-4-yl)-5-(piperazin-1-yl)pyrazolo[1,5-a]pyrimidine-3-carboxamide as a solid. $^1$H NMR (300 MHz, DMSO-d$_6$): δ 3.12-3.22 (m, 4H), 4.60-4.71 (m, 4H), 5.72-5.79 (m, 1H), 6.93-7.00 (m, 2H), 7.38-7.43 (m, 1H), 7.51-7.53 (d, J=6.9 Hz, 1H), 7.76 (s, 1H), 7.82-7.85 (m, 1H), 8.10 (s, 1H). MS [M+H]$^+$ 433.

Example 38

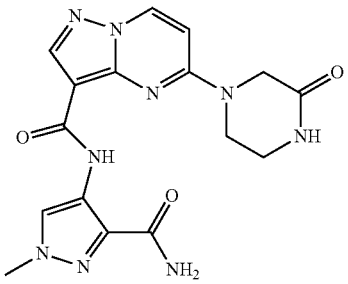 [SMILES: Cn1cc(NC(=O)c2cnn3ccc(N4CCNC(=O)C4)nc23)c(C(N)=O)n1]

N-(3-Carbamoyl-1-methyl-1H-pyrazol-4-yl)-5-(3-oxopiperazin-1-yl)pyrazolo[1,5-a]pyrimidine-3-carboxamide (IRAK4 IC$_{50}$=400 nM)

Step 1. Into a 50 mL round-bottom flask was placed a solution of ethyl 5-chloropyrazolo [1,5-a]pyrimidine-3-carboxylate (225 mg, 1.00 mmol) in acetonitrile (25 mL). This was followed by the addition of piperazin-2-one (300 mg, 3.00 mmol) and N,N-diisopropylethylamine (1 mL) at room temperature. The resulting solution was stirred overnight at 60° C. The resulting mixture was concentrated under reduced pressure. The residue was purified via a silica gel column eluting with dichloromethane/methanol (100:1-20:1). This resulted in ethyl 5-(3-oxopiperazin-1-yl)pyrazolo[1,5-a]pyrimidine-3-carboxylate as a solid.

Step 2. Into a 10 mL round-bottom flask was placed a solution of ethyl 5-(3-oxopiperazin-1-yl)pyrazolo[1,5-a]pyrimidine-3-carboxylate (100 mg, 0.35 mmol) in methanol/water (5 mL, 6:4). To the mixture was added lithium hydroxide (87 mg, 2.07 mmol). The resulting solution was stirred for 4 h at 45° C. The pH value of the solution was adjusted to 5 with hydrogen chloride (1M). The resulting mixture was concentrated under reduced pressure. This resulted in 5-[(2-aminoethyl)(carboxymethyl)amino]pyrazolo[1,5-a]pyrimidine-3-carboxylic acid as a solid.

Step 3. Into a 25 mL round-bottom flask was placed a solution of 5-[(2-aminoethyl)(carboxymethyl)amino]pyrazolo[1,5-a]pyrimidine-3-carboxylic acid (220 mg, 0.79 mmol) and 4-amino-1-methyl-1H-pyrazole-3-carboxamide (100 mg, 0.71 mmol) in N,N-dimethylformamide (5 mL). Then 4-dimethylaminopyridine (26.15 mg, 0.21 mmol), N,N-diisopropylethylamine (276 mg, 2.14 mmol) and (7-Azabenzotriazol-1-yloxy)tripyrrolidinophosphonium hexafluorophosphate (928 mg, 1.78 mmol) were added in order. The resulting solution was stirred for 3 h at 50° C. The resulting mixture was concentrated under reduced pressure. The crude product was purified by Prep-HPLC. This resulted in 1-methyl-4-C-5-(3-oxopiperazin-1-yl)pyrazolo[1,5-a]pyrimidine-3-1H-pyrazole-3,4-diamido as a solid. $^1$H NMR (400 MHz, DMSO-d$_6$): δ 3.38 (s, 2H), 3.90 (s, 3H), 4.28 (s, 4H), 6.82-6.84 (d, J=8.0 Hz, 1H), 7.28 (s, 1H), 7.56 (s, 1H), 8.29-8.37 (m, 3H), 8.79-8.81 (d, J=7.6 Hz, 1H), 10.57 (s, 1H). MS [M+H]$^+$ 384.

Example 39

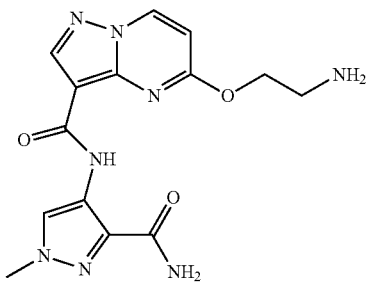 [SMILES: Cn1cc(NC(=O)c2cnn3ccc(OCCN)nc23)c(C(N)=O)n1]

5-(2-Aminoethoxy)-N-(3-carbamoyl-1-methyl-1H-pyrazol-4-yl)pyrazolo[1,5-a]pyrimidine-3-carboxamide (IRAK4 $IC_{50}$=9,200 nM)

Step 1. Into a 100 mL 3-necked round-bottom flask purged and maintained with an inert atmosphere of nitrogen were placed ethyl 5-hydroxypyrazolo [1,5-a] pyrimidine-3-carboxylate (414 mg, 2.00 mmol) in 1, 4-dioxane (40 mL), tert-butyl N-(2-hydroxyethyl)carbamate (480 mg, 2.98 mmol), and triphenylphosphine (1830 mg, 6.99 mmol) in order. This was followed by the addition of diisopropyl azodicarboxylate (1410 mg, 6.99 mmol) dropwise with stirring at 10° C. The resulting solution was stirred for 4 h at room temperature. The reaction was then quenched by the addition of 5 mL of water. The resulting mixture was concentrated under reduced pressure. The residue was dissolved in 500 mL of ethyl acetate. The resulting mixture was washed with 100 mL of sodium bicarbonate (aq). The organic phase was dried over anhydrous sodium sulfate, filtered and concentrated under reduced pressure. This resulted in ethyl 5-(2-[[(tert-butoxy)carbonyl]amino]ethoxy)pyrazolo[1,5-a]pyrimidine-3-carboxylate as an oil.

Step 2. Into a 100 mL round-bottom flask were placed methanol/water (20/20 mL) and ethyl 5-(2-[[(tert-butoxy)carbonyl]amino]ethoxy)pyrazolo[1,5-a]pyrimidine-3-carboxylate (350 mg, 1.00 mmol). To the solution was added lithium hydroxide (252 mg, 6.01 mmol). The resulting solution was stirred overnight at 45° C. The resulting mixture was concentrated under reduced pressure. The residue was dissolved in 100 mL of dichloromethane. The resulting solution was extracted with 2×200 mL of water and the aqueous layers combined. The pH value of the solution was adjusted to 5 with hydrogen chloride (37%). The resulting solution was extracted with 2×200 mL of dichloromethane and the organic layers were combined, dried over anhydrous sodium sulfate, filtered and concentrated under reduced pressure. The residue was purified via a silica gel column eluting with petroleum ether/ethyl acetate (150:1-10:1). This resulted in 5-(2-[[(tert-butoxy)carbonyl]amino]ethoxy)pyrazolo[1,5-a]pyrimidine-3-carboxylic acid as a solid.

Step 3. Into a 50 mL round-bottom flask were placed 5-(2-[[(tert-butoxy)carbonyl]amino]ethoxy)pyrazolo[1,5-a]pyrimidine-3-carboxylic acid (120 mg, 0.37 mmol) in acetonitrile (12 mL), 4-amino-1-methyl-1H-pyrazole-3-carboxamide (52 mg, 0.37 mmol), and N,N,N',N'-tetramethyl-O-(7-azabenzotriazol-1-yl)uronium hexafluorophospate (212 mg, 0.56 mmol). To the mixture was added N,N-diisopropylethylamine (96 mg, 0.74 mmol). The resulting solution was stirred for 4 h at 80° C. The resulting mixture was concentrated under reduced pressure. The residue was dissolved in 50 mL of dichloromethane. The resulting mixture was washed with 2×15 mL of brine. The organic phase was dried over anhydrous sodium sulfate, filtered and concentrated under reduced pressure. This resulted in tert-butyl N-[2-([3-[(3-carbamoyl-1-methyl-1H-pyrazol-4-yl)carbamoyl]pyrazolo[1,5-a]pyrimidin-5-yl]oxy)ethyl]carbamate as a solid.

Step 4. Into a 50-mL round-bottom flask were placed tert-butyl N-[2-([3-[(3-carbamoyl-1-methyl-1H-pyrazol-4-yl)carbamoyl]pyrazolo[1,5-a]pyrimidin-5-yl]oxy)ethyl]carbamate (150 mg, 0.34 mmol), dichloromethane (12 mL), and trifluoroacetic acid (4 mL). The resulting solution was stirred for 2 h at room temperature. The resulting mixture was concentrated under reduced pressure. The crude product was purified by Prep-HPLC. This resulted in 5-(2-aminoethoxy)-N-(3-carbamoyl-1-methyl-1H-pyrazol-4-yl)pyrazolo[1,5-a]pyrimidine-3-carboxamide trifluoroacetate as a solid. $^1$H NMR (400 MHz, DMSO-$d_6$): δ 3.40 (t, J=5.6 Hz, 2H), 3.86 (s, 3H), 4.58 (t, J=5.6 Hz, 2H), 6.29 (d, J=8 Hz, 1H), 8.05 (s, 1H), 8.17 (s, 1H), 8.34 (d, J=8 Hz, 1H). MS [M+H]$^+$ 345.

Example 40

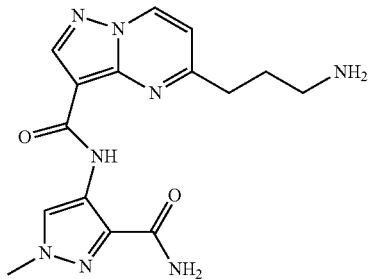 [SMILES: Cn1cc(NC(=O)c2cnn3ccc(CCCN)nc23)c(C(N)=O)n1]

5-(3-Aminopropyl)-N-(3-carbamoyl-1-methyl-1H-pyrazol-4-yl)pyrazolo[1,5-a]pyrimidine-3-carboxamide (IRAK4 $IC_{50}$=150 nM)

Step 1. Into a 50 mL round-bottom flask purged and maintained with an inert atmosphere of nitrogen were placed a solution of ethyl 5-chloropyrazolo[1,5-a]pyrimidine-3-carboxylate (300 mg, 1.33 mmol) in N,N-dimethylformamide (20 mL), tert-butyl N-(prop-2-yn-1-yl)carbamate (408 mg, 2.63 mmol), triethylamine (1.8 mL), copper (I) iodide (24 mg, 0.13 mmol), and Pd(PPh$_3$)$_2$Cl$_2$ (47.1 mg, 0.07 mmol). The resulting mixture was stirred for 5 h at room temperature. After concentrated under vacuum, the residue was treated with 30 mL of ethyl acetate. The resulting mixture was washed with 3×20 mL of water and 2×20 mL of sat. ammonium chloride. The organic phase was dried over sodium sulfate, concentrated, and filtered under reduced pressure. This resulted in ethyl 5-(3-[[(tert-butoxy)carbonyl]amino]prop-1-yn-1-yl)pyrazolo[1,5-a]pyrimidine-3-carboxylate as an oil.

Step 2. Into a 100 mL round-bottom flask purged and maintained with an atmosphere of H$_2$ were placed ethyl 5-(3-[[(tert-butoxy)carbonyl]amino]prop-1-yn-1-yl)pyrazolo[1,5-a]pyrimidine-3-carboxylate (600 mg, 1.74 mmol), palladium hydroxide on carbon (500 mg), and methanol (60 mL). The resulting mixture was stirred for 3 h at room temperature. The solids were filtered out. The resulting mixture was concentrated under reduced pressure. Then 2,3-Dichloro-5,6-dicyano-1,4-benzoquinone (600 mg, 2.64 mmol) and dichloromethane (60 mL) were added. The resulting solution was stirred for 12 h at room temperature. The residue was purified through a silica gel column eluting with ethyl acetate/petroleum ether (1:1). This resulted in ethyl 5-(3-[[(tert-butoxy)carbonyl]amino]propyl)pyrazolo[1,5-a]pyrimidine-3-carboxylate as an oil.

Step 3. A solution of ethyl 5-(3-[[(tert-butoxy)carbonyl]amino]propyl)pyrazolo[1,5-a]pyrimidine-3-carboxylate (260 mg, 0.75 mmol) and Lithium hydroxide (157 mg, 3.74 mmol) in methanol (18 mL) and water (12 mL) was stirred for 12 h at room temperature. The pH value of the solution was adjusted to 3 with hydrogen chloride. The resulting solution was extracted with 30 mL of dichloromethane and the organic layer was concentrated under reduced pressure. This resulted in 5-(3-[[(tert-butoxy)carbonyl]amino]propyl)pyrazolo[1,5-a]pyrimidine-3-carboxylic acid as an oil.

Step 4. Into a 25 mL round-bottom flask were placed 4-amino-1-methyl-1H-pyrazole-3-carboxamide (70 mg, 0.50 mmol), 5-(3-[[(tert-butoxy)carbonyl]amino]propyl)pyrazolo[1,5-a]pyrimidine-3-carboxylic acid (238 mg, 0.74 mmol), HATU (284 mg, 0.75 mmol), N,N-diisopropylethylamine (126 mL), and acetonitrile (10 mL). The resulting solution was stirred for 10 h at 60° C. in an oil bath. The resulting mixture was concentrated under reduced pressure. The residue was purified via a silica gel column eluting with ethyl acetate/petroleum ether (1:1-1:0) to give 150 mg (51%) of tert-butyl N-(3-[3-[(3-carbamoyl-1-methyl-1H-pyrazol-4-yl)carbamoyl]pyrazolo[1,5-a]pyrimidin-5-yl]propyl)carbamate as a brown solid.

Step 5. Into a 25 mL round-bottom flask were placed tert-butyl N-(3-[3-[(3-carbamoyl-1-methyl-1H-pyrazol-4-yl)carbamoyl]pyrazolo[1,5-a]pyrimidin-5-yl]propyl)carbamate (150 mg, 0.34 mmol), trifluoroacetic acid (2 mL), and dichloromethane (6 mL). The resulting solution was stirred for 2 h at room temperature. The resulting mixture was concentrated under reduced pressure. The crude product was purified by Prep-HPLC. This resulted in 5-(3-aminopropyl)-N-(3-carbamoyl-1-methyl-1H-pyrazol-4-yl)pyrazolo[1,5-a]pyrimidine-3-carboxamide trifluoroacetate as a solid. $^1$H NMR (400 MHz, DMSO-$d_6$): δ 2.23-2.30 (m, 2H), 2.87-2.92 (m, 2H), 3.08 (t, J=6.8 Hz, 2H), 3.94 (s, 3H), 7.22 (d, J=7.2 Hz, 1H), 7.61 (s, 1H), 7.73 (brs, 3H), 7.88 (s, 1H), 8.44 (s, 1H), 8.63 (s, 1H), 9.23 (d, J=6.8 Hz, 1H), 11.06 (s, 1H). MS [M+H]$^+$ 343.

Example 41

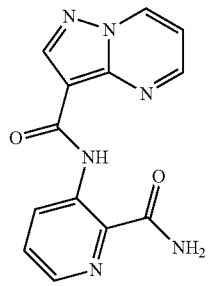 [SMILES: NC(=O)c1ncccc1NC(=O)c1cnn2cccnc12]

N-(2-Carbamoylpyridin-3-yl)pyrazolo[1,5-a]pyrimidine-3-carboxamide (IRAK4 IC$_{50}$=4,400 nM)

Thionyl chloride (8.92 mL, 123 mmol) was added to pyrazolo[1,5-a]pyrimidine-3-carboxylic acid (0.2 g, 1.2 mmol) and the mixture was stirred for 2 h at 80° C. The solvent was then removed under reduced pressure and the material was left on the high-vacuum for 3 h. The material was used without further purification.

To a stirred solution of 3-aminopyridine-2-carboxamide (0.04 g, 0.3 mmol) and the crude pyrazolo[1,5-a]pyrimidine-3-carbonyl chloride (0.064 g, 0.35 mmol) in dichloroethane (3 mL) were added 4-dimethylaminopyridine (3.6 mg, 0.029 mmol) and N,N-diisopropylethylamine (0.15 mL, 0.88 mmol). The reaction was allowed to stir for 18 h at 55° C. The solvent was removed under reduced pressure and the residue was purified by prep-HPLC to afford N-(2-carbamoylpyridin-3-yl)pyrazolo[1,5-a]pyrimidine-3-carboxamide trifluoroacetate. The material was then treated with 1 N HCl in a 1:1 mixture of acetonitrile:water and concentrated to afford N-(2-carbamoylpyridin-3-yl)pyrazolo[1,5-a]pyrimidine-3-carboxamide hydrochloride. $^1$H NMR (600 MHz, DMSO-$d_6$): δ 12.71 (s, 1H), 9.31 (dd, J=1.6, 7.0 Hz, 1H), 9.03 (dd, J=1.3, 8.6 Hz, 1H), 8.81 (dd, J=1.6, 4.1 Hz, 1H), 8.67 (s, 1H), 8.35 (s, 1H), 8.30 (dd, J=1.4, 4.4 Hz, 1H), 7.83 (s, 1H), 7.59 (dd, J=4.4, 8.6 Hz, 1H), 7.28 (dd, J=4.1, 7.0 Hz, 1H). MS [M+H]$^+$ 283.

The following examples were prepared in an analogous manner of that described in Example 41.

| Example # | IRAK4 IC$_{50}$ (nM) | Structure | IUPAC Name | Exact Mass [M + H]$^+$ |
|---|---|---|---|---|
| 42 | 370 | 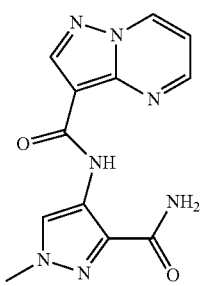 [SMILES: Cn1cc(NC(=O)c2cnn3cccnc23)c(C(N)=O)n1] | N-(3-carbamoyl-1-methyl-1H-pyrazol-4-yl)pyrazolo[1,5-a]pyrimidine-3-carboxamide | Calc'd 286, found 286 |

-continued

| Example # | IRAK4 IC$_{50}$ (nM) | Structure | IUPAC Name | Exact Mass [M + H]$^+$ |
|---|---|---|---|---|
| 43 | 27 | 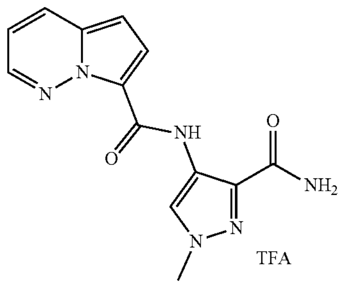 [SMILES: Cn1cc(NC(=O)c2ccc3cccnn23)c(C(N)=O)n1] | N-(3-carbamoyl-1-methyl-1H-pyrazol-4-yl)pyrrolo[1,2-b]pyridazine-7-carboxamide trifluoroacetate | Calc'd 285, found 285 |
| 44 | 59 | 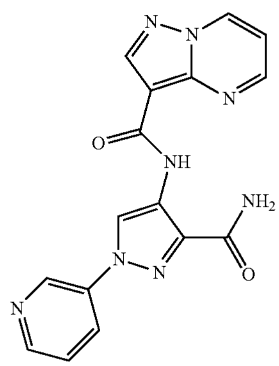 [SMILES: NC(=O)c1nn(-c2cccnc2)cc1NC(=O)c1cnn2cccnc12] | N-(3-carbamoyl-1-pyridin-3-yl-1H-pyrazol-4-yl)pyrazolo[1,5-a]pyrimidine-3-carboxamide | Calc'd 349, found 349 |
| 45 | 8,100 | 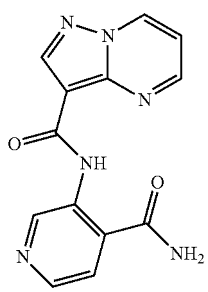 | N-(4-carbamoylpyridin-3-yl)pyrazolo[1,5-a]pyrimidine-3-carboxamide hydrochloride | Calc'd 283, found 283 |
| 46 | 670 | 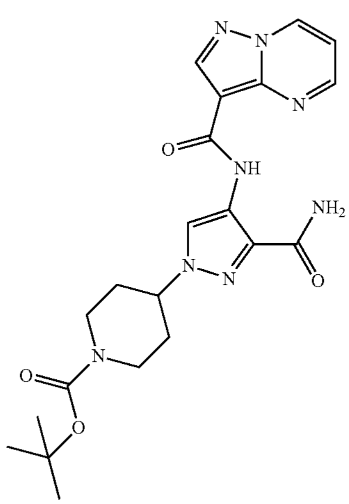 [SMILES: CC(C)(C)OC(=O)N1CCC(n2cc(NC(=O)c3cnn4cccnc34)c(C(N)=O)n2)CC1] | tert-butyl 4-{3-carbamoyl-4-[(pyrazolo[1,5-a]pyrimidin-3-ylcarbonyl)amino]-1H-pyrazol-1-yl}piperidine-1-carboxylate | Calc'd 455, found 455 |

-continued

| Example # | IRAK4 IC$_{50}$ (nM) | Structure | IUPAC Name | Exact Mass [M + H]$^+$ |
|---|---|---|---|---|
| 47 | 470 | 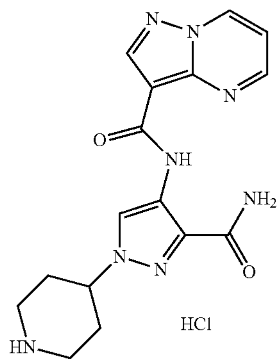 [SMILES: NC(=O)c1nn(C2CCNCC2)cc1NC(=O)c1cnn2cccnc12 ; Cl] | N-(3-carbamoyl-1-piperidin-4-yl-1H-pyrazol-4-yl)pyrazolo[1,5-a]pyrimidine-3-carboxamide hydrochloride | Calc'd 355, found 355 |
| 48 | 650 | 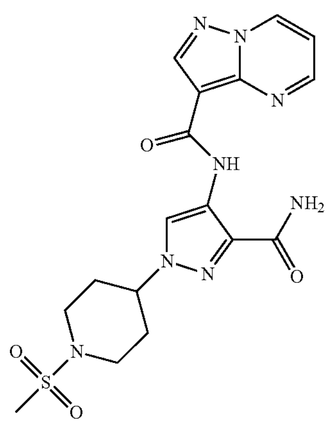 [SMILES: CS(=O)(=O)N1CCC(n2cc(NC(=O)c3cnn4cccnc34)c(C(N)=O)n2)CC1] | N-{3-carbamoyl-1-[1-(methylsulfonyl)piperidin-4-yl]-1H-pyrazol-4-yl}pyrazolo[1,5-a]pyrimidine-3-carboxamide | Calc'd 433, found 433 |
| 49 | 710 | 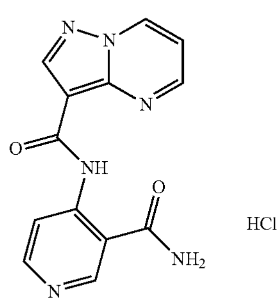 [SMILES: NC(=O)c1cnccc1NC(=O)c1cnn2cccnc12 ; Cl] | N-(3-carbamoylpyridin-4-yl)pyrazolo[1,5-a]pyrimidine-3-carboxamide hydrochloride | Calc'd 283, found 283 |
| 50 | 3,500 | 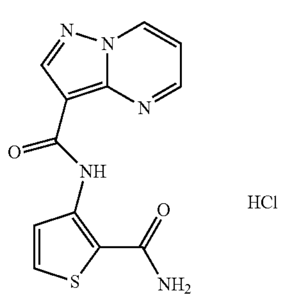 [SMILES: NC(=O)c1sccc1NC(=O)c1cnn2cccnc12 ; Cl] | N-(2-carbamoylthiophen-3-yl)pyrazolo[1,5-a]pyrimidine-3-carboxamide hydrochloride | Calc'd 288, found 288 |

-continued

| Example # | IRAK4 IC$_{50}$ (nM) | Structure | IUPAC Name | Exact Mass [M + H]$^+$ |
|---|---|---|---|---|
| 51 | 8,500 | 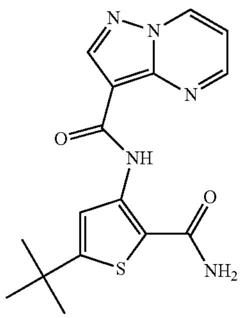 | N-(5-tert-butyl-2-carbamoylthiophen-3-yl)pyrazolo[1,5-a]pyrimidine-3-carboxamide hydrochloride | Calc'd 344, found 344 |
| 52 | 7,600 | 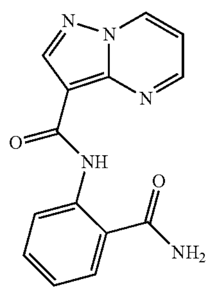 | N-(2-carbamoylphenyl)pyrazolo[1,5-a]pyrimidine-3-carboxamide hydrochloride | Calc'd 282, found 282 |
| 53 | 700 | 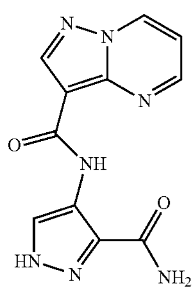 | N-(3-carbamoyl-1H-pyrazol-4-yl)pyrazolo[1,5-a]pyrimidine-3-carboxamide trifluoroacetate | Calc'd 272, found 272 |
| 54 | 310 | 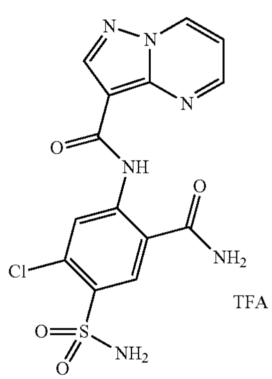 [SMILES: NC(=O)c1cc(S(N)(=O)=O)c(Cl)cc1NC(=O)c1cnn2cccnc12 ; "TFA"] | N-(2-carbamoyl-5-chloro-4-sulfamoylphenyl)pyrazolo[1,5-a]pyrimidine-3-carboxamide trifluoroacetate | Calc'd 395, found 395 |

| Example # | IRAK4 IC$_{50}$ (nM) | Structure | IUPAC Name | Exact Mass [M + H]$^+$ |
|---|---|---|---|---|
| 55 | >5,000 | 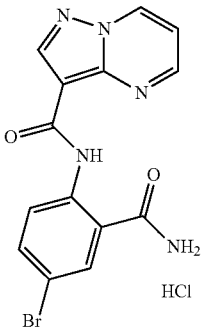 [SMILES: NC(=O)c1cc(Br)ccc1NC(=O)c1cnn2cccnc12 ; Cl] | N-(4-bromo-2-carbamoylphenyl)pyrazolo[1,5-a]pyrimidine-3-carboxamide hydrochloride | Calc'd 360, found 360 |

Example 56

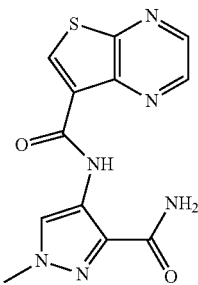 [SMILES: Cn1cc(NC(=O)c2csc3nccnc23)c(C(N)=O)n1]

N-(3-Carbamoyl-1-methyl-1H-pyrazol-4-yl)thieno[2,3-b]pyrazine-7-carboxamide (IRAK4 IC$_{50}$=69 nM)

To a microwave vial charged with 7-bromothieno[2,3-b]pyrazine (30.0 mg, 0.139 mmol), 4-amino-1-methyl-1H-pyrazole-3-carboxamide (21.5 mg, 0.153 mmol), Xantphos (12.1 mg, 0.021 mmol), sodium carbonate (73.9 mg, 0.697 mmol) and Pd(OAc)$_2$ (3.13 mg, 0.014 mmol) was added 1,4-dioxane (0.7 mL). The vial was sealed and then evacuated and back-filled with carbon monoxide gas three times using a balloon. The reaction mixture was brought to 90° C. and stirred under a carbon monoxide atmosphere for 18 hours. The reaction mixture was cooled to room temperature, diluted with DMSO (2 mL), filtered and purified by prep-HPLC affording N-(4-carbamoyl-1-methyl-1H-pyrrol-3-yl)thieno[2,3-b]pyrazine-7-carboxamide trifluoroacetate. $^1$H NMR (600 MHz, DMSO-d$_6$): δ 12.14 (s, 1H), 9.10 (s, 1H), 8.85 (d, J=2.4 Hz, 1H), 8.75 (d, J=2.4 Hz, 1H), 8.43 (s, 1H), 7.59 (s, 1H), 7.38 (s, 1H), 3.90 (s, 3H). MS [M+H]$^+$ 303.

The following example was prepared in an analogous manner of that described in Example 56.

| Example # | IRAK4 IC$_{50}$ (nM) | Structure | IUPAC Name | Exact Mass [M + H]$^+$ |
|---|---|---|---|---|
| 57 | 370 | 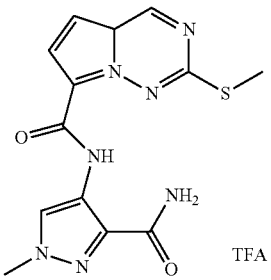 | N-(3-carbamoyl-1-methyl-1H-pyrazol-4-yl)-2-(methylsulfanyl)pyrrolo[2,1-f][1,2,4]triazine-7-carboxamide trifluoroacetate | Calc'd 332, found 332 |

Example 58

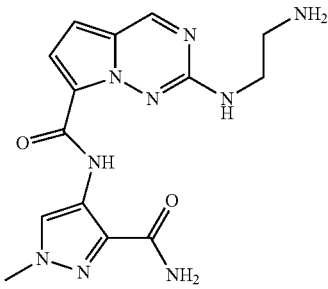 [SMILES: Cn1cc(NC(=O)c2ccc3cnc(NCCN)nn23)c(C(N)=O)n1]

2-[(2-Aminoethyl)amino]-N-(3-carbamoyl-1-methyl-1H-pyrazol-4-yl)pyrrolo[2,1-f][1,2,4]triazine-7-carboxamide (IRAK4 IC$_{50}$=0.9 nM)

Step 1. Into a 50 mL round bottom flask containing a solution of 7-bromo-2-(methylthio)pyrrolo[2,1-f][1,2,4]triazine (500 mg, 2.0 mmol) in dichloromethane (10 mL) was added m-chloroperoxybenzoic acid (400 mg, 2.3 mmol) at 0° C., and the reaction mixture was stirred at 0° C. for 20 min and then at room temperature for additional 30 min. The reaction mixture was diluted with dichloromethane and washed with water and brine solution successively. The organic layer was dried over anhydrous sodium sulfate, filtered and concentrated under reduced pressure. The residue was purified by column chromatography eluting with methanol in dichloromethane (3-5%) to afford 7-bromo-2-(methylsulfinyl)pyrrolo[2,1-f][1,2,4]triazine as a solid. $^1$H NMR (DMSO-d$_6$, 400 MHz): δ 9.25 (s, 1H), 7.38 (d, J=4.8 Hz, 1H), 7.31 (d, J=4.8 Hz, 1H), 2.96 (s, 3H). MS calc'd. [M+H]$^+$259.9, found 260.0.

Step 2. Into a 20 mL microwave vial containing a solution of 7-bromo-2-(methylsulfinyl)pyrrolo[2,1-f][1,2,4]triazine (380 mg, 1.45 mmol) in 2-methoxyethanol (5 mL) were added ethylenediamine (0.2 mL, 2.9 mmol) and N,N-diisopropylethylamine (0.4 mL, 2.2 mmol). The reaction mixture was subjected to microwave irradiation at 180° C. for 2 h. The solvent evaporated under reduced pressure and the residue was purified by flash chromatography eluting with methanol in dichloromethane (13-15%) to afford N-(7-bromopyrrolo[2,1-J][1,2,4]triazin-2-yl)ethane-1,2-diamine. $^1$H NMR (DMSO-d$_6$ 400 MHz): δ 8.78 (s, 1H), 7.5 (brs, 2H), 7.18-7.15 (m, 1H), 6.86 (d, J=4.7 Hz, 1H), 6.8 (d, J=4.7 Hz, 1H), 3.47 (t, J=6.1 Hz, 2H), 3.06 (t, J=6.1 Hz, 2H). MS calc'd [M+H]$^+$ 258.0, found 258.0.

Step 3. Into a 50 mL round bottom flask containing a solution of N-(7-bromopyrrolo[2,1-J][1,2,4]triazin-2-yl)ethane-1,2-diamine (280 mg, 1.0 mmol) in methanol (5 mL) was added triethylamine (0.4 mL, 2.8 mmol) followed by the addition of di-tert-butyl dicarbonate (0.4 mL, 1.7 mmol) at 0° C. and the reaction mixture was stirred at room temperature overnight. The solvent was removed under reduced pressure and the crude product was dissolved in ethyl acetate and washed with water and brine solution. The organic layer was dried over sodium sulfate, filtered, concentrated and purified by flash chromatography eluting with methanol in dichloromethane (3-5%) to afford tert-butyl (2-((7-bromopyrrolo[2,1-f][1,2,4]triazin-2-yl)amino)ethyl)carbamate as a solid. $^1$H NMR (DMSO-d$_6$, 400 MHz): δ 8.72 (s, 1H), 6.98 (brs, 1H), 6.88 (brs, 1H), 6.81 (d, J=4.8 Hz, 1H), 6.73 (d, J=4.8 Hz, 1H), 3.18-3.15 (m, 4H), 1.35 (s, 9H).

Step 4. Into a 25 mL tiny clave containing a solution of tert-butyl (2-((7-bromopyrrolo[2,1-f][1,2,4]triazin-2-yl)amino)ethyl)carbamate (300 mg, 0.9 mmol) in methanol (10 mL) was added sodium acetate (210 mg, 2.5 mmol) and the reaction mixture was degassed for 10 min with argon. 1,1'-bisdiphenylphosphino ferrocene (137 mg, 0.16 mmol) was added to the reaction mixture and the mixture was heated at 70° C. for 12 h under carbon monoxide atmosphere. The reaction mixture was cooled to room temperature and filtered through celite and the filtrate was concentrated under reduced pressure. The residue was purified by flash chromatography eluting with methanol in dichloromethane (0-5%) to afford methyl 2-((2-((tert-butoxycarbonyl)amino)ethyl)amino)pyrrolo[2,1-f][1,2,4]triazine-7-carboxylate. MS calc'd [M+H]$^+$ 336.2, found 336.4.

Step 5. Into a 50 mL round bottom flask containing a solution of methyl 2-((2-((tert-butoxycarbonyl)amino)ethyl)amino)pyrrolo[2,1-f][1,2,4]triazine-7-carboxylate (300 mg, 0.9 mmol) in tetrahydrofuran (2 mL) and water (4 mL) was added lithium hydroxide (115 mg, 2.7 mmol) and stirred at room temperature for 4-5 h. The reaction mixture was diluted with water and washed with ethyl acetate. The aqueous layer was cooled to 0° C. and the reaction mixture was acidified by using dilute hydrochloric acid (3 mL). The solid precipitated was filtered and dried under vacuum and the residue was purified by flash chromatography eluting with methanol in dichloromethane (5-10%) to afford 2-((2-((tert-butoxycarbonyl)amino)ethyl)amino)pyrrolo[2,1-f][1,2,4]triazine-7-carboxylic acid as solid. $^1$H NMR (DMSO-d$_6$ 300 MHz): δ 8.98 (s, 1H), 7.24 (brs, 1H), 7.12 (d, J=4.7 Hz, 1H), 6.85 (brs, 1H), 6.76 (d, J=4.7 Hz, 1H), 4.47-4.42 (m, 2H), 3.18-3.16 (m, 2H), 1.33 (s, 9H). MS calc'd [M+H]$^+$ 320.1, found 320.2.

Step 6. Into a 10 mL round bottom flask containing a solution of 2-((2-((tert-butoxycarbonyl)amino)ethyl)amino)pyrrolo[2,1-f][1,2,4]triazine-7-carboxylic acid (40 mg, 0.1 mmol) in acetonitrile (2 mL) were added 4-amino-1-methyl-1H-pyrazole-3-carboxamide (20 mg, 0.15 mmol) and HATU (70 mg, 0.2 mmol) followed by the addition of N,N-diisopropylethylamine (0.05 mL, 0.25 mmol) and stirred at 60° C. for 12 h. The reaction mixture was cooled to room temperature, diluted with water and extracted with ethyl acetate (3×25 mL). The combined organic fractions were washed with water and brine, dried over anhydrous sodium sulfate, filtered and concentrated. The residue was purified by flash chromatography eluting with methanol in dichloromethane (2-5%) to afford tert-butyl (2-((7-((3-carbamoyl-1-methyl-1H-pyrazol-4-yl)carbamoyl)pyrrolo[2,1-f][1,2,4]triazin-2-yl)amino)ethyl)carbamate as a solid. MS calc'd [M+H]$^+$ 444.2, found 444.4.

Step 7. Into a 50 mL round bottom flask containing a solution of tert-butyl (2-((7-((3-carbamoyl-1-methyl-1H-pyrazol-4-yl)carbamoyl)pyrrolo[2,1-f][1,2,4]triazin-2-yl)amino)ethyl)carbamate (40 mg, 0.1 mmol) in 1,4-dioxane (0.5 mL) was added HCl in dioxane (2 mL) and stirred at room temperature of 1 h. The solvent was evaporated under reduced pressure and the residue was purified by preparative HPLC to afford 2-((2-aminoethyl)amino)-N-(3-carbamoyl-1-methyl-1H-pyrazol-4-yl)pyrrolo[2,1-f][1,2,4]triazine-7-carboxamide trifluoroacetate as a solid. $^1$H NMR (CD$_3$OD, 400 MHz): δ 8.91 (s, 1H), 8.42 (s, 1H), 7.37 (d, J=5.2 Hz, 1H), 6.86 (d, J=4.8 Hz, 1H), 3.99-3.96 (m, 5H), 3.24 (t, J=5.6 Hz, 2H). MS calc'd [M+H]$^+$ 344.2, found 344.2.

The following examples were prepared in an analogous manner of that described in Example 58.

| Example # | IRAK4 IC$_{50}$ (nM) | Structure | IUPAC Name | Exact Mass [M + H]$^+$ |
|---|---|---|---|---|
| 59 | 2 | 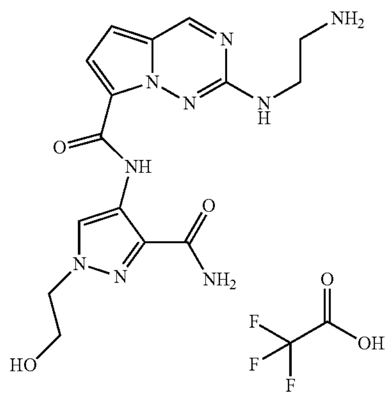 [SMILES: NCCNc1ncc2ccc(C(=O)Nc3cn(CCO)nc3C(N)=O)n2n1 ; O=C(O)C(F)(F)F] | 2-[(2-aminoethyl)amino]-N-[3-carbamoyl-1-(2-hydroxyethyl)-1H-pyrazol-4-yl]pyrrolo[2,1-f][1,2,4]triazine-7-carboxamide trifluoroacetate | Calc'd 374.2, found 374.4 |
| 60 | 3 | 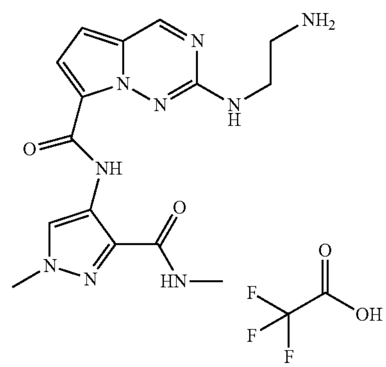 | 2-[(2-aminoethyl)amino]-N-[1-methyl-3-(methylcarbamoyl)-1H-pyrazol-4-yl]pyrrolo[2,1-f][1,2,4]triazine-7-carboxamide trifluoroacetate | Calc'd 358.2, found 358.4 |
| 61 | 0.7 | 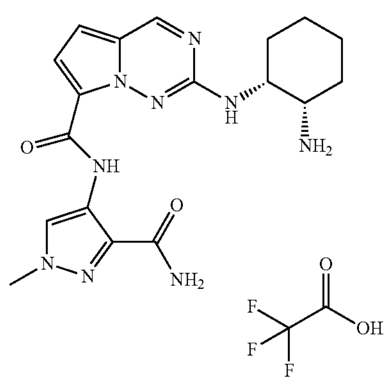 [SMILES: Cn1cc(NC(=O)c2ccc3cnc(N[C@@H]4CCCC[C@@H]4N)nn23)c(C(N)=O)n1 ; O=C(O)C(F)(F)F] | 2-{[(1R,2S)-2-aminocyclohexyl]amino}-N-(3-carbamoyl-1-methyl-1H-pyrazol-4-yl)pyrrolo[2,1-f][1,2,4]triazine-7-carboxamide trifluoroacetate | Calc'd 398.2, found 398.4 |
| 62 | 1 | 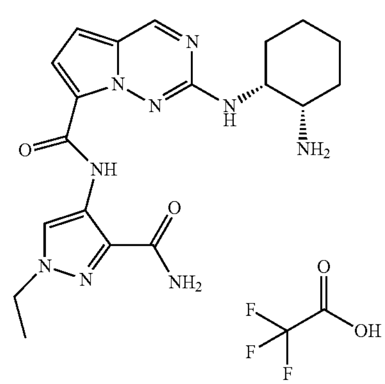 [SMILES: CCn1cc(NC(=O)c2ccc3cnc(N[C@@H]4CCCC[C@@H]4N)nn23)c(C(N)=O)n1 ; O=C(O)C(F)(F)F] | 2-{[(1R,2S)-2-aminocyclohexyl]amino}-N-(3-carbamoyl-1-ethyl-1H-pyrazol-4-yl)pyrrolo[2,1-f][1,2,4]triazine-7-carboxamide trifluoroacetate | Calc'd 412.2, found 412.4 |

-continued

| Example # | IRAK4 IC$_{50}$ (nM) | Structure | IUPAC Name | Exact Mass [M + H]$^+$ |
|---|---|---|---|---|
| 63 | 3 | 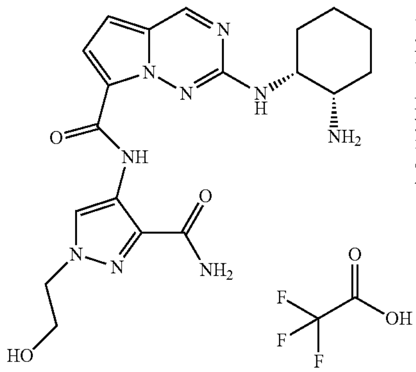 | 2-{[(1R,2S)-2-aminocyclohexyl]amino}-N-[3-carbamoyl-1-(2-hydroxyethyl)-1H-pyrazol-4-yl]pyrrolo[2,1-f][1,2,4]triazine-7-carboxamide trifluoroacetate | Calc'd 428.2, found 428.2 |
| 64 | 13 | 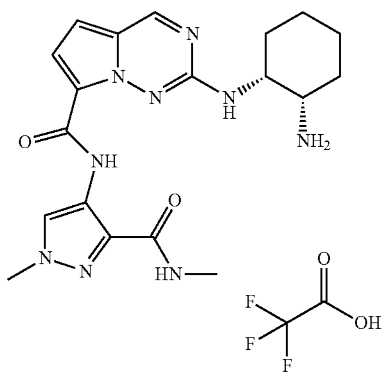 | 2-{[(1R,2S)-2-aminocyclohexyl]amino}-N-[1-methyl-3-(methylcarbamoyl)-1H-pyrazol-4-yl]pyrrolo[2,1-f][1,2,4]triazine-7-carboxamide trifluoroacetate | Calc'd 412.2, found 412.2. |
| 65 | 63 | 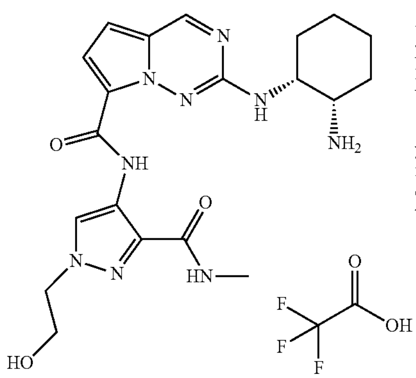 | 2-{[(1R,2S)-2-aminocyclohexyl]amino}-N-[1-(2-hydroxyethyl)-3-(methylcarbamoyl)-1H-pyrazol-4-yl]pyrrolo[2,1-f][1,2,4]triazine-7-carboxamide trifluoroacetate | Calc'd 442.2, found 442.4 |
| 66 | 6 | 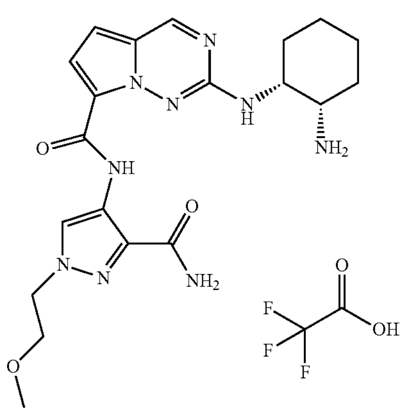 [SMILES: COCCn1cc(NC(=O)c2ccc3cnc(N[C@@H]4CCCC[C@@H]4N)nn23)c(C(N)=O)n1 ; O=C(O)C(F)(F)F] | 2-{[(1R,2S)-2-aminocyclohexyl]amino}-N-[3-carbamoyl-1-(2-methoxyethyl)-1H-pyrazol-4-yl]pyrrolo[2,1-f][1,2,4]triazine-7-carboxamide trifluoroacetate | Calc'd 442.2, found 442.4 |

Biological Data

Compounds of the instant invention were tested by the assay described below and were found to have IRAK4 inhibitory activity. Data is shown for all compounds in the representative table(s) and Examples. Other assays are known in the literature and could be readily performed by those of skill in the art.

IRAK4 Kinase Assay

The kinase activity of IRAK4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 μL reaction mixture contains 10 mM TriHCl, pH 7.2, 0.5 nM GST tagged IRAK4 (SignalChem), 100 nM fluorescent peptide substrate (RP7030, Molecular Devices), 100 μM ATP, 1 mM DDT, 1 mM MgCl$_2$, and 0.01% Tween 20. The reaction is initiated by the addition of ATP. After incubation for 30 minutes at 25° C., 60 μL of Progressive IMAP Reagent (Molecular Devices) is added to stop the reaction. Change in RP7030's FP is determined by a FP reader (Analyst HT, LJL BioSystems).

What is claimed is:

1. A compound according to Formula I:

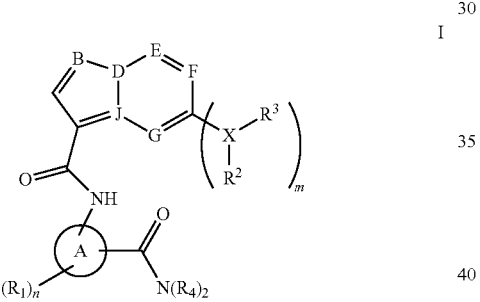

I wherein:
B is N; D is N; E is CH; F is CH; G is N; and J is C;
X is O, S, CH$_2$ or N;
m is 0 or 1; n is 0, 1 or 2;
Ring A is pyridinyl, pyrazolyl, thiophenyl, furanyl or phenyl,
R$_1$ is independently selected from (C$_1$-C$_4$)alkyl, pyrimidine, piperidine and phenyl, each optionally substituted with (C$_1$-C$_4$)alkyl, OH, halo, O(C$_1$-C$_4$)alkyl, methyl-piperidine, S(O)$_2$R$_c$, C(O)N(R$_b$)$_2$, or C(O)O(C$_1$-C$_4$) alkyl;
R$_2$ is absent or H and R$_3$ is independently selected from: (C$_1$-C$_4$)alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, N(R$_b$)$_2$, oxopyrrolidinyl, or morpholinyl, or R$_2$ and R$_3$ can be taken together with the nitrogen to which they are attached to form piperazine or morpholine, each optionally substituted with oxo;
R$_4$ is independently H or methyl;
R$_b$ is independently selected from H and (C$_1$-C$_4$)alkyl; and
R$_c$ is methyl;
or a pharmaceutically acceptable salt thereof.

2. A compound according to claim 1 of Formula II:

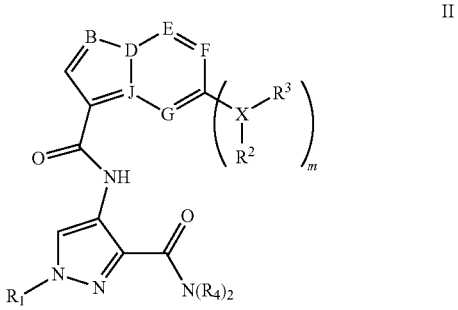

II wherein:

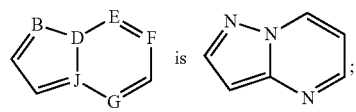

is

X is O, S, CH$_2$ or N;
m is 0 or 1;
R$_1$ is independently selected from (C$_1$-C$_4$)alkyl, pyrimidine, piperidine and phenyl, each optionally substituted with (C$_1$-C$_4$)alkyl, OH, halo, O(C$_1$-C$_4$) alkyl, methyl-piperidine, S(O)$_2$R$_c$, C(O)N(R$_b$)$_2$, or C(O)O(C$_1$-C$_4$)alkyl;
R$_2$ is absent or H and R$_3$ is independently selected from: (C$_1$-C$_4$)alkyl, pyranyl, cyclopentyl, cyclohexyl, cycloheptyl, thiopyranyl, pyrazolyl, piperidinyl, morpholinyl, piperazinyl each optionally substituted with one or more substituents independently selected from halo, OH, oxo, N(R$_b$)$_2$, oxopyrrolidinyl, or morpholinyl, or R$_2$ and R$_3$ can be taken together with the nitrogen to which they are attached to form piperazine or morpholine, each optionally substituted with oxo;
R$_4$ is independently H or methyl;
R$_b$ is independently selected from H and (C$_1$-C$_4$)alkyl; and
R$_c$ is methyl;
or a pharmaceutically acceptable salt thereof.

3. A compound according to claim 1, or a pharmaceutically acceptable salt thereof, wherein Ring A is pyrazole.

4. A compound according to claim 1, or a pharmaceutically acceptable salt thereof, wherein X is N.

5. A compound according to claim 2, or a pharmaceutically acceptable salt thereof, wherein X is N.

6. A compound which is selected from:
5-{[(3R,4R)-4-aminotetrahydro-2H-pyran-3-yl]amino}-N-(3-carbamoyl-1-methyl-1H-pyrazol-4-yl)pyrazolo[1,5-a]pyrimidine-3-carboxamide;
5-{[(3R,4R)-3-aminotetrahydro-2H-pyran-4-yl]amino}-N-(3-carbamoyl-1-methyl-1H-pyrazol-4-yl)pyrazolo[1,5-a]pyrimidine-3-carboxamide;
5-{[(1R,2R)-2-amino-3,3-difluorocyclohexyl]amino}-N-(3-carbamoyl-1-methyl-1H-pyrazol-4-yl)pyrazolo[1,5-a]pyrimidine-3-carboxamide;
5-{[(3S,4S)-3-amino-1,1-dioxidotetrahydro-2H-thiopyran-4-yl]amino}-N-(3-carbamoyl-1-methyl-1H-pyrazol-4-yl)pyrazolo[1,5-a]pyrimidine-3-carboxamide;

5-{[(3R,4R)-4-amino-1,1-dioxidotetrahydro-2H-thiopyran-3-yl]amino}-N-(3-carbamoyl-1-methyl-1H-pyrazol-4-yl)pyrazolo[1,5-a]pyrimidine-3-carboxamide;
5-{[(1 S,2R)-2-aminocyclohexyl]amino}-N-(3-carbamoyl-1-pyridin-3-yl-1H-pyrazol-4-yl)pyrazolo[1,5-a]pyrimidine-3-carboxamide;
5-{[(1 S,2R)-2-aminocyclohexyl]amino}-N-(3-carbamoyl-1-methyl-1H-pyrazol-4-yl)pyrazolo[1,5-a]pyrimidine-3-carboxamide;
5-{[(1R,2R)-2-aminocyclohexyl]amino}-N-(3-carbamoyl-1-methyl-1H-pyrazol-4-yl)pyrazolo[1,5-a]pyrimidine-3-carboxamide;
5-{[(1R,2S)-2-aminocyclohexyl]amino}-N-(3-carbamoyl-1-methyl-1H-pyrazol-4-yl)pyrazolo[1,5-a]pyrimidine-3-carboxamide;
5-{[(1 S,2R)-2-aminocyclohexyl]amino}-N-[3-carbamoyl-1-(1-methylpiperidin-3-yl)-1H-pyrazol-4-yl]pyrazolo[1,5-a]pyrimidine-3-carboxamide;
5-[(2-aminoethyl)amino]-N-(3-carbamoyl-1-pyridin-3-yl-1H-pyrazol-4-yl)pyrazolo[1,5-a]pyrimidine-3-carboxamide;
5-[(2-aminocyclopentyl)amino]-N-(3-carbamoyl-1-methyl-1H-pyrazol-4-yl)pyrazolo[1,5-a]pyrimidine-3-carboxamide;
5-[(2-aminocycloheptyl)amino]-N-(3-carbamoyl-1-methyl-1H-pyrazol-4-yl)pyrazolo[1,5-a]pyrimidine-3-carboxamide;
N-(3-carbamoyl-1-methyl-1H-pyrazol-4-yl)-5-(pyrrolidin-3-ylamino)pyrazolo[1,5-a]pyrimidine-3-carboxamide;
N-(3-carbamoyl-1-methyl-1H-pyrazol-4-yl)-5-(piperidin-3-ylamino)pyrazolo[1,5-a]pyrimidine-3-carboxamide;
5-{[(1 S,2R)-2-aminocyclohexyl]amino}-N-[1-methyl-3-(methylcarbamoyl)-1H-pyrazol-4-yl]pyrazolo[1,5-a]pyrimidine-3-carboxamide;
5-{[(1 S,2R)-2-aminocyclohexyl]amino}-N-[3-(dimethylcarbamoyl)-1-methyl-1H-pyrazol-4-yl]pyrazolo[1,5-a]pyrimidine-3-carboxamide;
5-{[(1 S,2R)-2-aminocyclohexyl]amino}-N-{3-carbamoyl-1-[1-(methylsulfonyl)piperidin-4-yl]-1H-pyrazol-4-yl}pyrazolo[1,5-a]pyrimidine-3-carboxamide;
5-{[(1 S,2R)-2-aminocyclohexyl]amino}-N-[3-carbamoyl-1-(1-methylpiperidin-4-yl)-1H-pyrazol-4-yl]-7aH-pyrazolo[4,3-b]pyridine-3-carboxamide;
5-{[(1 S,2R)-2-aminocyclohexyl]amino}-N-{3-carbamoyl-1-[1-(methylsulfonyl)piperidin-3-yl]-1H-pyrazol-4-yl}pyrazolo[1,5-a]pyrimidine-3-carboxamide;
5-{[(1R,2S)-2-aminocyclohexyl]amino}-N-(3-carbamoyl-1-ethyl-1H-pyrazol-4-yl)pyrazolo[1,5-a]pyrimidine-3-carboxamide;
5-{[(1R,2 S)-2-aminocyclohexyl]amino}-N-[3-carbamoyl-1-(1-methylethyl)-1H-pyrazol-4-yl]pyrazolo[1,5-a]pyrimidine-3-carboxamide;
5-{[(1R,2 S)-2-aminocyclohexyl]amino}-N-[3-carbamoyl-1-(2-hydroxyethyl)-1H-pyrazol-4-yl]pyrazolo[1,5-a]pyrimidine-3-carboxamide;
5-{[(1R,2 S)-2-aminocyclohexyl]amino}-N-[3-carbamoyl-1-(2-methoxyethyl)-1H-pyrazol-4-yl]pyrazolo[1,5-a]pyrimidine-3-carboxamide;
5-{[(1R,2S)-2-aminocyclohexyl]amino}-N-{3-carbamoyl-1-[(1-methylpiperidin-3-yl)methyl]-1H-pyrazol-4-yl}pyrazolo[1,5-a]pyrimidine-3-carboxamide;
N-(3-carbamoyl-1-methyl-1H-pyrazol-4-yl)-5-(cyclohexylamino)pyrazolo[1,5-a]pyrimidine-3-carboxamide;
N-(3-carbamoyl-1-methyl-1H-pyrazol-4-yl)-5-[(2-hydroxycyclohexyl)amino]pyrazolo[1,5-a]pyrimidine-3-carboxamide;
5-[(2-aminoethyl)amino]-N-(3-carbamoyl-1-methyl-1H-pyrazol-4-yl)pyrazolo[1,5-a]pyrimidine-3-carboxamide;
N-(3-carbamoyl-1-methyl-1H-pyrazol-4-yl)-5-{[(5-oxopyrrolidin-3-yl)methyl]amino}pyrazolo[1,5-a]pyrimidine-3-carboxamide;
N-(3-carbamoyl-1-methyl-1H-pyrazol-4-yl)-5-morpholin-4-ylpyrazolo[1,5-a]pyrimidine-3-carboxamide;
N-(3-carbamoyl-1-methyl-1H-pyrazol-4-yl)-5-piperazin-1-ylpyrazolo[1,5-a]pyrimidine-3-carboxamide;
5-{[(1R,2S)-2-aminocyclohexyl]amino}-N-[1-(2-amino-2-oxoethyl)-3-carbamoyl-1H-pyrazol-4-yl]pyrazolo[1,5-a]pyrimidine-3-carboxamide;
N-{3-carbamoyl-1-[4-(methylsulfamoyl)phenyl]-1H-pyrazol-4-yl}-5-piperazin-1-ylpyrazolo[1,5-a]pyrimidine-3-carboxamide;
N-(3-carbamoyl-1-pyridin-4-yl-1H-pyrazol-4-yl)-5-piperazin-1-ylpyrazolo[1,5-a]pyrimidine-3-carboxamide;
N-(5-carbamoyl-1-pyridin-4-yl-1H-pyrazol-4-yl)-5-piperazin-1-ylpyrazolo[1,5-a]pyrimidine-3-carboxamide;
N-(3-carbamoyl-1-pyridin-3-yl-1H-pyrazol-4-yl)-5-piperazin-1-ylpyrazolo[1,5-a]pyrimidine-3-carboxamide;
N-(3-carbamoyl-1-pyridin-2-yl-1H-pyrazol-4-yl)-5-piperazin-1-ylpyrazolo[1,5-a]pyrimidine-3-carboxamide;
N-(3-carbamoyl-1-methyl-1H-pyrazol-4-yl)-5-(3-oxopiperazin-1-yl)pyrazolo[1,5-a]pyrimidine-3-carboxamide;
5-(2-aminoethoxy)-N-(3-carbamoyl-1-methyl-1H-pyrazol-4-yl)pyrazolo[1,5-a]pyrimidine-3-carboxamide;
5-(3-aminopropyl)-N-(3-carbamoyl-1-methyl-1H-pyrazol-4-yl)pyrazolo[1,5-a]pyrimidine-3-carboxamide;
N-(2-carbamoylpyridin-3-yl)pyrazolo[1,5-a]pyrimidine-3-carboxamide;
N-(3-carbamoyl-1-methyl-1H-pyrazol-4-yl)pyrazolo[1,5-a]pyrimidine-3-carboxamide;
N-(3-carbamoyl-1-pyridin-3-yl-1H-pyrazol-4-yl)pyrazolo[1,5-a]pyrimidine-3-carboxamide;
N-(4-carbamoylpyridin-3-yl)pyrazolo[1,5-a]pyrimidine-3-carboxamide;
tert-butyl 4-{3-carbamoyl-4-[(pyrazolo[1,5-a]pyrimidin-3-ylcarbonyl)amino]-1H-pyrazol-1-yl}piperidine-1-carboxylate;
N-(3-carbamoyl-1-piperidin-4-yl-1H-pyrazol-4-yl)pyrazolo[1,5-a]pyrimidine-3-carboxamide;
N-{3-carbamoyl-1-[1-(methylsulfonyl)piperidin-4-yl]-1H-pyrazol-4-yl}pyrazolo[1,5-a]pyrimidine-3-carboxamide;
N-(3-carbamoylpyridin-4-yl)pyrazolo[1,5-a]pyrimidine-3-carboxamide;
N-(2-carbamoylthiophen-3-yl)pyrazolo[1,5-a]pyrimidine-3-carboxamide;
N-(5-tert-butyl-2-carbamoylthiophen-3-yl)pyrazolo[1,5-a]pyrimidine-3-carboxamide;
N-(2-carbamoylphenyl)pyrazolo[1,5-a]pyrimidine-3-carboxamide;
N-(3-carbamoyl-1H-pyrazol-4-yl)pyrazolo[1,5-a]pyrimidine-3-carboxamide;
N-(2-carbamoyl-5-chloro-4-sulfamoylphenyl)pyrazolo[1,5-a]pyrimidine-3-carboxamide; and
N-(4-bromo-2-carbamoylphenyl)pyrazolo[1,5-a]pyrimidine-3-carboxamide;
or a pharmaceutically acceptable salt thereof.

7. A pharmaceutical composition comprising a pharmaceutical carrier and a therapeutically effective amount of a compound of claim 1.

8. A method for treating an inflammatory disease which comprises administering to a mammal in need thereof a therapeutically effective amount of a compound of claim 1 or a pharmaceutically acceptable salt thereof.

9. The method according to claim 8 wherein the inflammatory A disease is selected from rheumatoid arthritis, and inflammatory bowel disease.

10. A method of treating an inflammatory disease which comprises administering a therapeutically effective amount of a compound of claim 1, or a pharmaceutically acceptable salt thereof, in combination with a second therapeutic agent.

11. The method of claim 10 wherein the second therapeutic agent is an anti-inflammatory agent.

\* \* \* \* \*